(12) United States Patent
Robinson et al.

(10) Patent No.: US 9,168,527 B2
(45) Date of Patent: Oct. 27, 2015

(54) ELECTROKINETIC FLUIDIC SYSTEM

(75) Inventors: Nathaniel D. Robinson, Kolmården (SE); Per Erlandsson, Linköping (SE)

(73) Assignee: LunaMicro AB, Kolmarden (SE)

( * ) Notice: Subject to any disclaimer, the term of this patent is extended or adjusted under 35 U.S.C. 154(b) by 507 days.

(21) Appl. No.: 13/580,343

(22) PCT Filed: Feb. 22, 2011

(86) PCT No.: PCT/SE2011/050199
§ 371 (c)(1),
(2), (4) Date: Aug. 21, 2012

(87) PCT Pub. No.: WO2011/102801
PCT Pub. Date: Aug. 25, 2011

(65) Prior Publication Data
US 2012/0312384 A1    Dec. 13, 2012

Related U.S. Application Data

(60) Provisional application No. 61/306,586, filed on Feb. 22, 2010.

(30) Foreign Application Priority Data

Feb. 22, 2010    (SE) ...................................... 1050168

(51) Int. Cl.
*G01N 27/453* (2006.01)
*B01L 3/00* (2006.01)
(Continued)

(52) U.S. Cl.
CPC ....... *B01L 3/50273* (2013.01); *B01L 3/502707* (2013.01); *B03C 5/02* (2013.01); *F04B 19/006* (2013.01); *B01L 2300/0816* (2013.01); *B01L 2300/161* (2013.01); *B01L 2400/0418* (2013.01);
(Continued)

(58) Field of Classification Search
CPC .................. G01N 27/44747; G01N 27/44791; B03C 5/00–5/028
See application file for complete search history.

(56) References Cited

U.S. PATENT DOCUMENTS 5,092,972 A    3/1992    Ghowsi
5,358,616 A    10/1994    Ward
(Continued)

FOREIGN PATENT DOCUMENTS

EP    2151501 A1 *    2/2010
JP    2002-148236    5/2002
(Continued)

OTHER PUBLICATIONS

Office Action for corresponding Japanese Application No. 2012-553852 mailed Aug. 5, 2014.
(Continued)

*Primary Examiner* — Alexander Noguerola
(74) *Attorney, Agent, or Firm* — Polster, Lieder, Woodruff & Lucchesi, LLC

(57) ABSTRACT

An electrokinetic fluidic system (100, 100', 100") for controlling liquid flow in e.g. a lab-on-a-chip system (200) comprising a first and a second electrode (10, 10') said first and second electrode comprising a polymer based or oxide based conductive, electrochemically active electrode material, said electrode material being adapted to be subjected to an electrochemical reaction when in use in said electrokinetic fluid system (100).

20 Claims, 12 Drawing Sheets

Figure 2A:
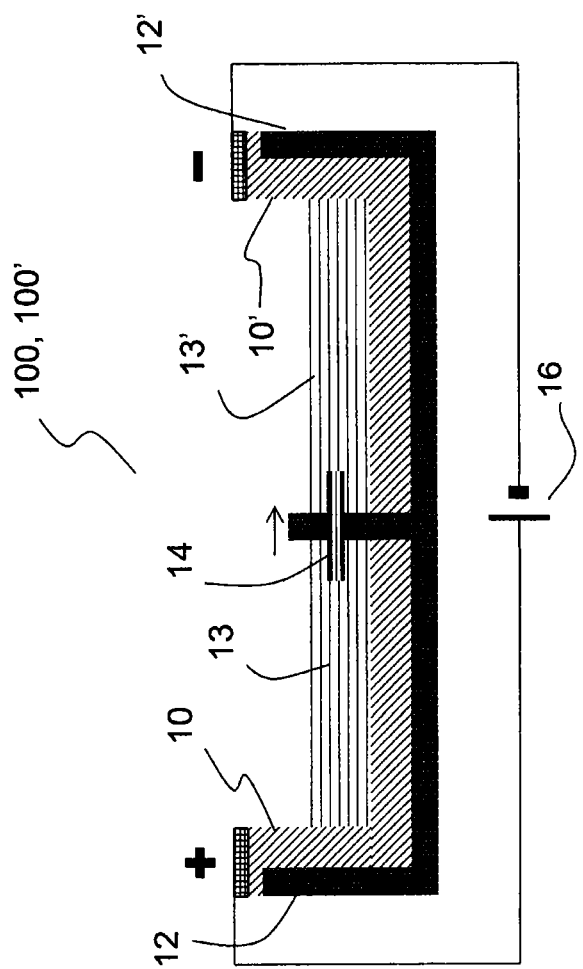

(51) Int. Cl.
*B03C 5/02* (2006.01)
*F04B 19/00* (2006.01)
*G01N 27/447* (2006.01)

(52) U.S. Cl.
CPC ....... *B03C 2201/26* (2013.01); *G01N 27/44791* (2013.01); *Y10T 137/0391* (2015.04); *Y10T 137/206* (2015.04)

(56) References Cited

U.S. PATENT DOCUMENTS

| | | | |
|---|---|---|---|
| 6,287,440 | B1 | 9/2001 | Arnold et al. |
| 6,613,211 | B1 * | 9/2003 | McCormick et al. ......... 204/601 |
| 6,642,069 | B2 | 11/2003 | Armgarth et al. |
| 2002/0166592 | A1 | 11/2002 | Liu et al. |
| 2005/0092692 | A1 | 5/2005 | Hishida et al. |
| 2005/0189225 | A1 | 9/2005 | Liu et al. |
| 2007/0009366 | A1 | 1/2007 | Myers et al. |
| 2007/0151856 | A1 * | 7/2007 | Fazzio et al. ................. 204/605 |
| 2010/0034667 | A1 | 2/2010 | Khamizov et al. |

FOREIGN PATENT DOCUMENTS

| | | |
|---|---|---|
| JP | 2004-538128 A | 12/2004 |
| JP | 2005-87868 A | 4/2005 |
| JP | 2005-531756 A | 10/2005 |
| JP | 2005-351686 A | 12/2005 |
| JP | 2007-085998 A | 4/2007 |
| JP | 2007-256261 | 10/2007 |
| JP | 2009-516173 A | 4/2009 |
| JP | 2009-264786 A | 11/2009 |
| WO | 00/28315 | 5/2000 |
| WO | 02/076585 A1 | 10/2002 |
| WO | 03/018484 A1 | 3/2003 |
| WO | 03/101592 A1 | 12/2003 |
| WO | 2007-046485 A1 | 4/2007 |
| WO | 2007/059167 A2 | 5/2007 |
| WO | 2007/090232 A1 | 8/2007 |
| WO | 2007/112864 A1 | 10/2007 |

OTHER PUBLICATIONS

Decision of Rejection for corresponding Japanese Application No. 2012-553852 mailed May 19, 2015.
A. Plecis, J. Tazid, A. Pallandre, P. Martinhon, C. Deslouis, Y. Chen, A. M. Haghiri-Gosnet, "Flow field effect transistors with polarisable interface for EOF tunable microfluidic separation devices" online article, The Royal Society of Chemistry, pp. 1245-1253, Feb. 2010.
Prasanna Chandrasekhar, "Conducting Polymers: Fundamentals and Applications—A Practical Approach", Kluwer Academic Publishers, pp. 4-23, 370-429, 626-635.
Gerhard Kossmehl, Gunnar Engelmann, (ed Denis Fichou), "Handbook of Oligo- and Polythiophenes", chapter 10.8, Application of Electrically Conductive Polythiophenes, Wiley-VCH Verlag GmbH, Weinheim, Germany, pp. 502-507, 1999.
J. C. Gustafsson, B. Liedberg, O. Inganas, "In situ spectroscopic investigations of electrochromism and ion transport in a poly (3, 4-ethylenedioxythiophene) electrode in a solid state electrochemical cell", Solid State Ionics 69, Elsevier Science B.V., pp. 145-152, Apr. 14, 1994.
J. Rouquerol, D. Avnir, C. W. Fairbridge, D. H. Everett, J. H. Haynes, N. Pernicone, J. D. F. Ramsay, K. S. W. Sing, and K. K. Unger, "Recommendations for the Characterization of Porous Solids", International Union of Pure and Applied Chemistry, vol. 66, No. 8, pp. 1739-1758, 1994.
Brian J. Kirby, "Kirby Research Group at Cornell: Microfluidics and Nanofluidics", Cambridge University Press, Cornell University College of Engineering Kirby Research Group, online posting pp. 1-13, Jul. 16, 2012.
Mitsuyoshi Onoda, Hiroshi Nakayama, Shigenori Morita, and Katsumi Yoshino, "Properties of Electronically Cation-Doped Poly(isothianaphthene)", J. Electrochem Soc., vol. 141, No. 2, pp. 338-341, Feb. 1994.
Alan G. Macdiarmind and Arthur J. Epstein, ""Synthetic Metals": A Novel Role for Organic Polymers", Makromol. Chem., Macromol. Symp. 51, Huthig & Wepf Verlag, Basel, pp. 11-28, 1991.
Edward Cohen, Edgar Gutoff, "Modern Coating and Drying Technology", chapter 1—Choosing the Coating Method, VCH, pp. 1-21.
Petra Mela, Niels R. Tas, Erwin J. W. Berenschot, Jan Van Nieuwkasteele, Albert Van Den Berg, "Electrokinetic pumping and detection of low-volume flows in nanochannels", Electrophoresis, Wiley-VCH Verlag GmbH & Co. KGaA, Weinheim, pp. 3687-3693, 2004.
Philippe Schottland, Kyukwan Zong, Carleton L. Gaupp, Barry C. Thompson, Christopher A. Thomas, Irina Giurgiu, Roberta Hickman, Khalil A. Abboud, and John R. Reynolds, "Poly(3,4-alkylenedioxypyrrole)s: Highly Stable Electronically Conducting and Electrochromic Polymers", Macromolecules 2000, 33, American Chemical Society, pp. 7051-7061, 2000.
Herbert A. Pohl, "Dielectrophoresis: The behavior of neutral matter in nonuniform electric fields", Cambridge University Press, pp. 1-19.
Bjorn Winter-Jensen, Jun Chen, Keld West, and Gordon Wallace, "Vapor Phase Polymerization of Pyrrole and Thiophene Using Iron(III) Sulfonates as Oxidizing Agents", Macromolecules 2004, 37, American Chemical Society, pp. 5930-5935, published on web Jul. 10, 2004.
International Search Report for PCT application PCT/SE2011/050199 mailed Jun. 1, 2011.
Written Opinion for PCT application PCT/SE2011/050199 mailed Jun. 1, 2011.

* cited by examiner

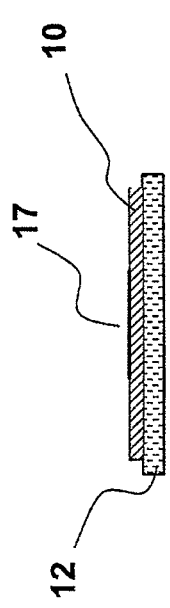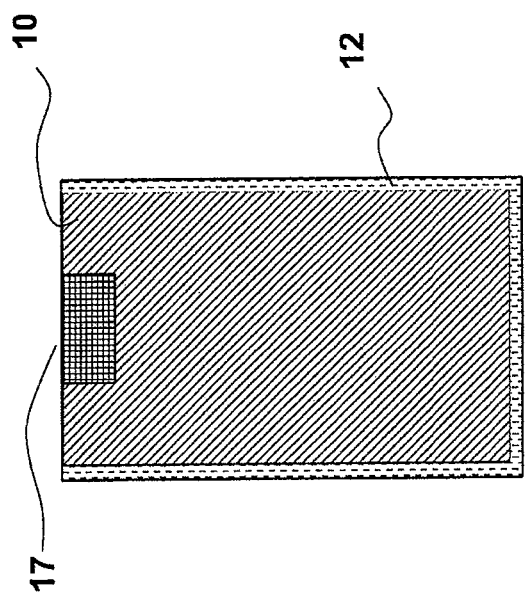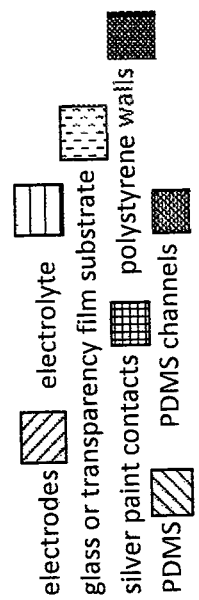
Fig 1A
Fig 1B

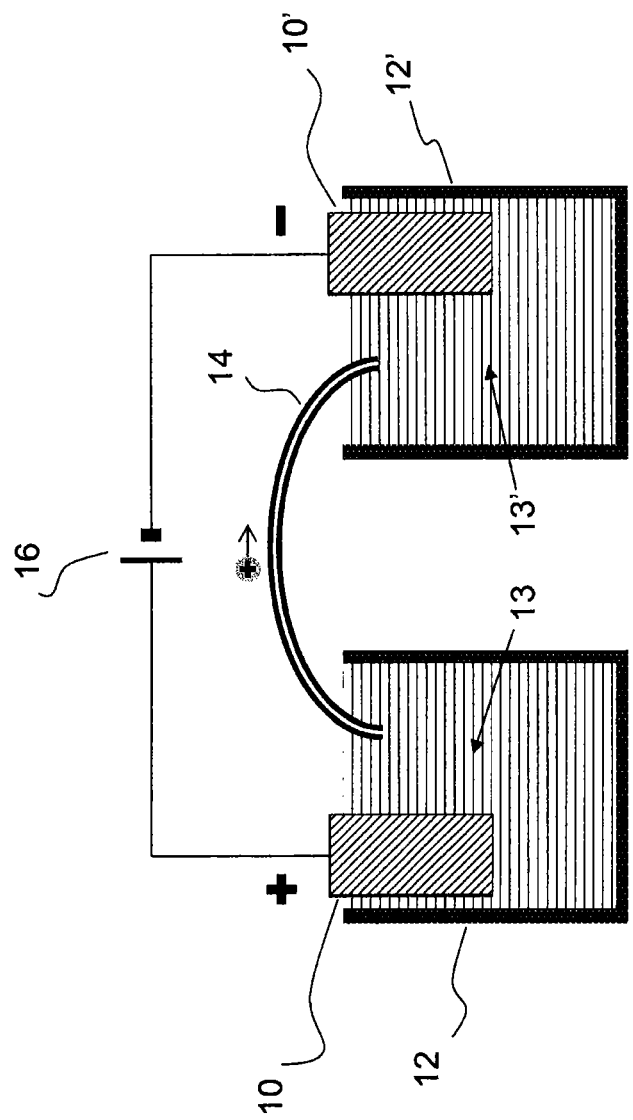

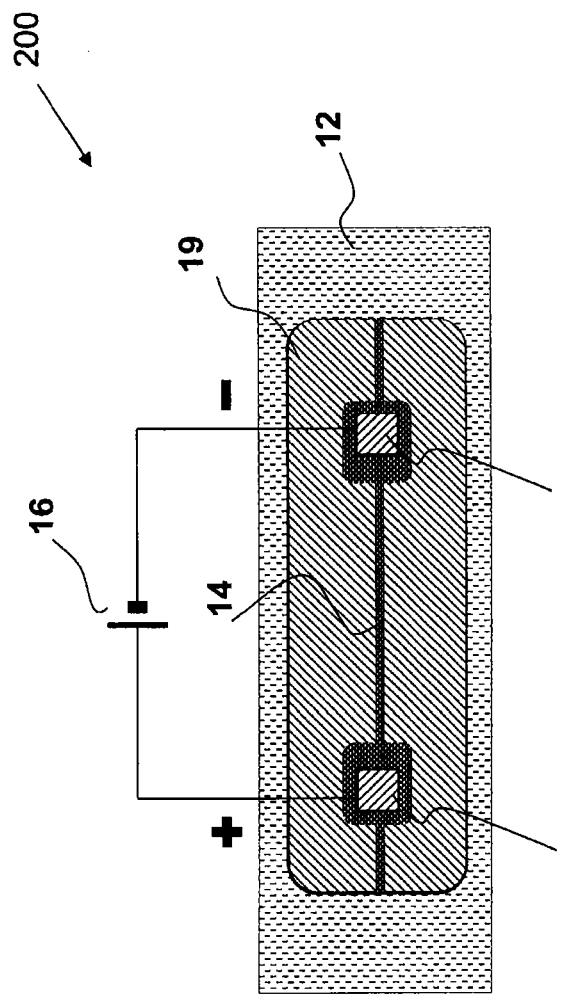
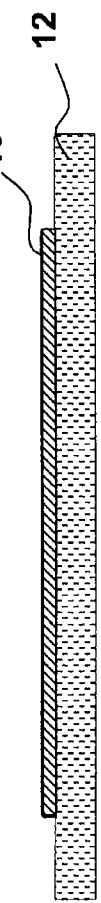
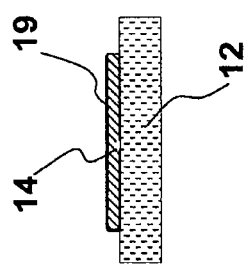
Fig 4A
Fig 4B
Fig 4C

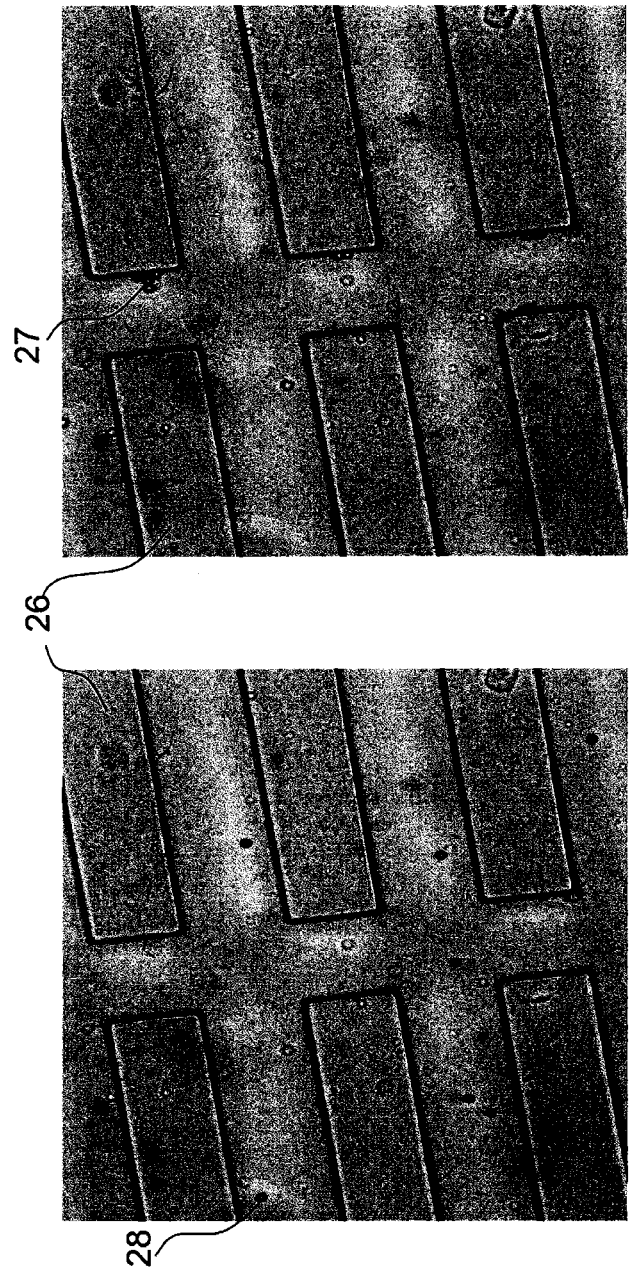

ELECTROKINETIC FLUIDIC SYSTEM

CROSS-REFERENCE TO RELATED APPLICATIONS

This is a national stage application under 35 U.S.C. §371 of International Application PCT/SE2011/050199 filed Feb. 22, 2011. The present application claims priority from U.S. Provisional Application Ser. No. 61/306,586 filed on Feb. 22, 2010, and from Swedish Application No. 1050168-2 filed on Feb. 22, 2010. All of these applications are hereby incorporated herein by reference.

TECHNICAL FIELD OF THE INVENTION

The present invention relates to an electrokinetic fluidic system (100, 100', 100") for controlling liquid flow in e.g. a lab-on-a-chip system (200) comprising a first and a second electrode (10, 10') and to an electrokinetic fluid system comprising such an electrode. The electrokinetic fluid system is configured to control liquid flow and/or particle flow in a microfluidic system for applications in biotechnology, analytical chemistry, etc.

BACKGROUND OF THE INVENTION

Microfluidic lab-on-a-chip (LOC) systems are stated to revolutionize the healthcare industry by replacing large-scale chemistry/biology laboratories with hand-held automated diagnostic tools, bringing sophisticated diagnostic techniques to patients' homes and third world countries. The LOC systems' capacity to handle and analyze minute sample volumes in the femtoliter to picoliter range and ability to test hundreds of samples simultaneously extends tremendous potential for areas like drug discovery and remote healthcare. Small, e.g. credit card-sized or smaller, self-contained LOC devices are expected to make complex medical diagnoses easy to perform.

One important component of sophisticated LOC devices is the microfluidic pump, which moves a liquid sample between the various mixers, separators, reactors and detectors required to perform an analysis. The ease-of-manufacture and small size of electrokinetic pumps, e.g. electroosmotic (EO) pumps, are advantages for their use as microfluidic pumps in LOC systems.

However, electrokinetic pumps usually produce gas bubbles; e.g. hydrogen gas, oxygen gas, hydrogen peroxide and/or protons (acid) or hydroxide ions (base), at the pump electrodes due to electrochemical reactions in the electrolyte when an electrical field is applied to the electrolyte. Such electrochemical reactions are undesirable. Gases, when generated, can quickly break the electrical connection between the liquid sample, e.g. an aqueous sample, and the electrode, affecting the mobility of the liquid sample within the electrokinetic pump. Further, generated acid, base and/or hydrogen peroxide can disturb or destroy the sensitive sample materials, e.g. proteins, to be studied.

The problem with today's electrokinetic pumps stems from the metal electrodes used to apply and maintain an electric field in the electrolyte. Maintaining an electric field in an electrolyte requires electrochemistry to be performed in or on the electrolyte at the pump electrodes, effectively transducing the current from electronic to ionic charge carriers or vice versa. These electrochemical processes often consume the electrolyte, e.g. water, itself, producing electrochemical by-products, such as $H^+$, $OH^-$, $H_2O_2$, $H_2$ gas and $O_2$ gas in the case of the electrolyte being water, which by-products can be detrimental to sensitive biological or chemical sample materials being transported or separated. In the specific case of microfluidic devices, the production of $H_2$ or $O_2$ gas at a pump electrode can create a bubble which, eventually, blocks liquid from reaching the pump electrode and renders the microfluidic device useless. Further, the formation of $H^+$, $OH^-$ may change the pH of the electrolyte at the pump electrodes which may negatively affect the sample material to be studied. Furthermore, the electrochemical reaction may cause consumption of, or otherwise disturb the environment of, the reagents or analyte used.

The state-of-the-art for LOC devices of today offers three alternatives to solve the above-mentioned problems.

A first proposed solution uses an external pump. However, the external pump is often considerably larger than the LOC itself, and thereby precluding a self-contained device.

In a second proposed solution, an internal mechanical pump, such as an electro-mechanical, pneumatic or hydraulic pump, is used. However, such internal mechanical pumps are often very expensive to manufacture.

According to a third proposed solution, an internal electroosmotic pump is used. An advantage with the internal electroosmotic pump is that it has no moving parts, and is therefore easy to manufacture.

Unfortunately, as previously described, internal electroosmotic pumps usually generate unwanted by-products in the electrolyte at the pump electrodes which impede their application in a LOC device or negatively impact the sample to be tested. The side reactions generating these unwanted by-products can be mediated by adding a chemical buffer, e.g. a buffer to keep the pH at a desired level, to the solutions to be pumped, to a sample to be tested, separated, or to a carrier electrolyte. However, these chemicals can sometimes interfere with the materials being studied or transported, and are therefore undesirable. Further, the use of a buffer implies an additional cost for manufacturing and operating the device.

Alternatively, very large volume containers surrounding the metal electrodes can minimize the impact of the by-products through dilution. However, this alternative is undesirable in microfluidic LOC devices due to the size of the large volume containers and due to the size requirements on LOC devices.

In another alternative, a metal that can be oxidized and dissolved in solution (such as Ag, etc.) is used in one or both electrodes. The metal is oxidized at the positive electrode and released into solution as a cation, which is transported with the fluid in the pump to the negative electrode, where it is reduced again. The challenge with this type of system is the sensitivity of biological samples and proteins to the Ag cation. For example, a Ag cation is often toxic to bacteria or living cells.

The US application U.S. patent application Ser. No. 11/168,779, published as US 2007/0009366 A1, to Myers et al., describes an electroosmotic pump wherein the problem of gas bubble formation is overcome by providing a sheath around at least one of the electrodes. The sheath being configured to pass ions, to reduce the passage of gas bubbles formed at the electrode and to collect the formed gas bubbles inside the sheath. Further, when the gas pressure is built up within the sheath, the gas bubbles are discarded from the electroosmotic pump.

The U.S. Pat. No. 6,287,440 B1, to Sandia Corporation, discloses a method and an apparatus for eliminating electrokinetic pump failure caused by gas bubbles formed by electrochemical decomposition of an electrolyte thereby blocking current flow through the electrokinetic pump. In the method and apparatus disclosed in U.S. Pat. No. 6,287,440 B1, the electrodes are placed away from the pressurized region of the pump, such that gas generated at the electrodes can escape into a larger buffer reservoir and not into the high pressure region of the pump where the gas bubbles can interrupt current flow.

The US application U.S. patent application Ser. No. 11/102,063, published as US 2005/0189225 A1, to Liu et al., describes a microfluidic system comprising an electroosmotic flow pumping means having a bubble-free electrode to prevent electrolysis and bubble formation. The bubble-free electrode comprises a tube loaded with an immobilized polymer and provides a means to apply voltage across pump channels while preventing passages of fluid through it, and a means to avoid electrolysis and bubble formation in or close to the microfluidic channels.

Drawbacks with these types of electrokinetic pumps are that they are difficult to include in a miniaturized device as they often requires a larger footprint. Furthermore, the complex geometries required and use of several different materials complicate their manufacture. Further drawbacks are bubbles generated at the pumping electrodes, as well as changes in pH caused by hydrolysis.

The present invention aims to overcome the drawbacks of the prior art electrokinetic fluid systems and to provide an electrokinetic fluid system suitable for a micofluidic lab-on-a-chip (LOC) system.

SUMMARY OF THE INVENTION

The present invention overcomes the drawbacks of the prior art systems by employing an electrochemically active, conducting material as the electrode material. Thereby, an electrokinetic fluid system, e.g. an electrokinetic pumping system such as an electroosmotic pumping system, or e.g. an electrokinetic separation system such as an electrophoretic system, is provided that nearly eliminates the oxidation or reduction of the electrolyte, e.g. water, and hence also eliminates the production of the by-products, making such electrokinetic fluid systems ideally suited for LOC applications. Laboratory-scale or industrial-scale applications of electrokinetic systems can also benefit from the present invention.

By performing electrochemistry, e.g. oxidation or reduction, on the stationary electrode material itself, rather than in the electrolyte, the undesired electrochemical by-products described above can be minimized or eliminated.

Some advantages with the present invention are that the undesired electrochemical by-products at the electrodes are minimized or eliminated, that there is a reduced (or no) need for adding buffers or other chemical additives to the electrolyte or the sample in order to keep the pH at a desired level thus minimising the risk of impairing the sample to be tested, and that the electrokinetic fluid system of the present invention is simple to manufacture. To preserve pH in the electrolyte is of importance for samples sensitive for pH-changes such as e.g. biological samples and solutions. To be able to keep the pH at a stable level in the electrolyte it should not be consumed by electrolysis. The system of the invention allows the necessary electrochemical reaction to occur on and also within the electrodes.

Thus, one object of the present invention provides an electrokinetic fluidic system (100, 100', 100") for controlling liquid flow, characterized in that it comprises a first and a second electrode (10, 10') arranged in a respective vessel (12, 12'), said electrodes comprise a polymer based or oxide based conductive, electrochemically active electrode material, said electrode material being adapted to be subjected to an electrochemical reaction when in use in said electrokinetic fluid system (100), and further a channel (14) arranged as a passageway between the two vessels, said channel allowing flow of electrolyte (13, 13') between said two vessels (12, 12').

In further embodiments the electrokinetic fluidic system (100) for controlling liquid flow is characterized in that the electrode material is arranged at least at a surface of said electrode (10,10'), said surface being facing an electrolyte (13,13') when the electrode (10,10') is in use in said electrokinetic fluid system (100).

In still further embodiments, the electrokinetic fluidic system (100) according to the invention is characterized in that the conductive, electrochemically active electrode material conducts electricity in at least one reduction-oxidation state, is electrochemically switchable, does not break apart and does not release toxic substances into the electrolyte (13,13').

The electrokinetic fluidic system (100) according to the invention is characterized in that the conductive, electrochemically active electrode material is selected from the group of pi-conjugated polymers.

Further embodiments are wherein the electrokinetic fluidic system (100) according to the invention, characterized in that the conductive, electrochemically active electrode material comprises a any of the pi-conjugated polymers selected from the group consisting of polyacetylenes, polypyrroles, polythiophenes, polyanilines, poly(p-phenylene sulfide), poly(p-phenylene vinylene)s, polyindole, polypyrene, polycarbazole, polyazulene, polyazepine, polyfluorenes, polynaphthalene and polyisothianaphthalenes, a copolymer thereof, or a mixture thereof.

Further embodiments are wherein the electrokinetic fluidic system (100) according to the invention, characterized in that the conductive, electrochemically active electrode material comprises a metal oxide such as a Vanadium oxide or Tungsten oxide.

Further embodiments are wherein the electrokinetic fluidic system (100) according to the invention, wherein said channel (14) is at least one capillary allowing flow of electrolyte (13, 13').

Further embodiments are wherein the electrokinetic fluidic system (100) according to the invention, wherein said channel (14) is a porous material of solid or semi-solid material, or a membrane, allowing flow of electrolyte (13, 13').

A membrane is a layer of material which serves as a barrier between two phases and remains impermeable to specific particles, molecules, or substances when exposed to the action of a driving force. Some components are allowed passage by the membrane into a permeate stream, whereas others are retained by it and accumulate in the retentate stream.[1]

Membranes can be of various thicknesses, with homogeneous or heterogeneous structure. Membrane can also be classified according to their pore diameter. According to IUPAC, there are three different types of pore size classifications: microporous (dp<2 nm), mesoporous (2 nm<dp<50 nm) and macroporous (dp>50 nm).[2] Membranes can be neutral or charged, and particles transport can be active or passive. The latter can be facilitated by pressure, concentration, chemical or electrical gradients of the membrane process. Membranes can be generally classified into three groups: inorganic, polymeric or biological membranes. These three types of membranes differ significantly in their structure and functionality.[3]

Further embodiments are wherein the electrokinetic fluidic system (100) according to the invention, wherein said channel is formed of glass, e.g. silicon oxides, a polyanion such as poly(styrenesulfonate), or a polycation such as protonated poly-L-lysine.

Further embodiments are wherein the walls of said channel are charged, often via the dissociation of a salt or deprotonation of an alcohol group. For example, the silanol on silicon oxides often deprotonates, leaving a negatively charged oxygen atom at the surface. Salts of polyanions such as sodium poly(styrenesulfonate) dissociate, leaving the immobile sulfonate ion at the surface. Another example is the protonation of poly-L-lysine at appropriate pH values, causing the stationary interface to have a net positive charge.

The electrodes used in the electrokinetic device have limited capacity, meaning that one or both electrodes will be "depleted" when nearly fully doped (oxidized) or dedoped (neutral). Switching the sign of the charge on the walls of the capillary/porous material from negative to positive (or vice versa) allows the polarity of the electrodes driving the flow to be reversed while the direction of the flow stays the same. In this manner, small electrodes can drive a large volume of fluid, or can operate continuously.

Further embodiments are wherein the walls of said channel are not charged, such as polyimide, particularly in the case where electrophoretic separation, rather than generating electroosmotic flow, is desired.

Further embodiments are wherein the charge on the walls of said channel can be controlled by an electric potential, such as described in Plecis et al. "Flow field effect transistors with polarisable interface for EOF tunable microfluidic separation devices". Lab on a Chip, DOI: 10.1039/b921808d, and patents U.S. Pat. No. 5,092,972-A, U.S. Pat. No. 5,358,616-A, WO0028315.

Further embodiments are wherein said channel is <200 μm in diameter. Further embodiment with parallel channels, porous materials etc. are given herein.

Further embodiments are wherein the electrokinetic fluidic system (100) according to the invention, further comprises an electric field generating device (16).

Another object of the present invention is to provide a method to control liquid flow in an electrokinetic fluidic system, the method comprising
 a) applying an electric field to a first and a second electrode (10, 10') arranged in a respective vessel (12, 12'), said electrodes comprise a polymer based or oxide based conductive, electrochemically active electrode material, said electrode material being adapted to be subjected to an electrochemical reaction when in use in said electrokinetic fluid system (100),
 b) controlling said electric field by means of an electric field device (16), allowing a controlled flow of electrolyte (13, 13').

Further embodiments are wherein the electrokinetic fluidic system is according to the present invention.

Further embodiments are wherein the method further comprises the steps of controlling flow of charged species in said electrolyte.

Further embodiments are wherein the method according to the invention, further comprises the steps of controlling flow of non-charged species in said electrolyte.

Further embodiments are wherein said flow of charged and non-charged molecules in said electrolyte (13, 13') is controlled by controlling said electric field by means of an electric field device (16), allowing a controlled flow of electrolyte (13, 13').

Still a further object of the present invention is to provide a method allowing controlled flow of charged and non-charged molecules in an electrokinetic fluidic system as provided herein, the method comprising
 a) providing a charged or non-charged molecule in the electrolyte (13, 13') in a first or a second vessel (12, 12'),
 b) applying an electric field to a first and a second electrode (10, 10') arranged in a respective vessel (12, 12'), said electrodes comprise a polymer based or oxide based conductive, electrochemically active electrode material, said electrode material being adapted to be subjected to an electrochemical reaction when in use in said electrokinetic fluid system (100), and wherein the conductive, electrochemically active electrode material is selected from the group of pi-conjugated polymers.
 c) controlling said electric field by means of an electric field device (16), allowing a controlled flow of electrolyte (13, 13'), thereby allowing a controlled flow of a charged or non-charged molecule in said electrolyte (13, 13').

In a specific case the electric field generated not only is used to drive or control flow in the system, but is also used to separate species in a mixture based on their net charge and mobility.

As used herein, mobility is intended to mean the velocity per charge per units of electric field. I.e. doubling the charge on a molecule with a fixed mobility causes it to move twice as fast (assuming field is constant).

A species' net charge is the total charge said species has. It can be either positive (+) or negative (−), or zero, i.e. neutral, charge. Furthermore, the net charge may be more than one unity, for example $Ca^{2+}$ with a net charge of 2. The net charge of a species, such as a charged molecule, influences how the species moves in an electric field.

Further, the shape and size influences how the species moves. A bulky molecule, such as a branched sugar molecules or a large protein moves differently if charged or not. Further, a small net charge may not be sufficient to allow a small electric field to transport a bulky and large species significantly. Thus, size, branching and net charge all influence the transport of a species.

Further, when the net charge is zero, it may be distributed non-uniformly (e.g., due to an external electric field or a zwitterion), in which case the species is said to be polarized and if the molecule is able to polarize when influenced by an electric field this may also affect the transport of said species in an electric field.

Thus, in a more complex system comprising different species in an electric field, each species often moves at its own, unique rate, allowing them to be separated from each other.

Further, EOF, as generated by the electroosmotic pump claimed in this patent, can be used to drive species through a separation media with a stationary or fixed phase such as a column packed with beads, a monolith, etc., such that the species are separated based upon their interaction with the stationary phase rather than on their relative mobility and charge.

Still a further object of the present invention is to provide a method allowing controlled flow and a controlled separation of a mixture of charged and/or non-charged species in an electrokinetic fluidic system as provided herein, the method comprising
 a) providing a mixture of charged or non-charged molecule in the electrolyte (13, 13') in a first or a second vessel (12, 12'),
 b) applying an electric field to a first and a second electrode (10, 10') arranged in a respective vessel (12, 12'), said electrodes comprise a polymer based or oxide based conductive, electrochemically active electrode material, said electrode material being adapted to be subjected to an electrochemical reaction when in use in said electrokinetic fluid system (100), c) controlling said electric field by means of an electric field device (16), allowing a controlled flow of electrolyte (13, 13'), thereby allowing a controlled flow of a charged or non-charged molecule in said electrolyte (13, 13'), thereby separating a mixture of charged and/or non-charged species.

Further objects of the present invention are to provide microfluidic lab-on-a-chip system (200) for controlling liquid flow, comprising an electrokinetic fluid system (100) according to the present invention.

Still further objects of the present invention is to provide microfluidic lab-on-a-chip system (200) for controlling flow of charged or non-charged species, comprising an electrokinetic fluid system (100) according to the present invention.

Further objects of the present invention provide the use of the electrokinetic fluid system (100) according to the invention in a lab-on-a-chip system (200).

Still further objects provide use of the electrokinetic fluid system (100) according to the present invention for controlling liquid flow in a lab-on-a-chip system (200).

Still further objects provide the use of the electrokinetic fluid system (100) according to the present invention for controlling flow of one or more charged or non-charged species in a lab-on-a-chip system (200).

Still even further objects provide a kit comprising the electrokinetic fluidic system (100) according to any of claims 1-12, and optionally, instructions for its use.

SHORT DESCRIPTION OF THE DRAWINGS

Embodiments of the present invention will be described in more detail with reference to the accompanying drawings in which electrodes, electrolyte, glass or transparency film substrate, silver paint contacts, polystyrene walls, PDMS, PDMS channels are all seen in each fill in pattern shown in FIGS. 1A and 1B, and in which:

FIG. 1 schematically illustrates an embodiment of an electrode (10, 10') of the present invention; 1A shows a side view and 1B shows a top view. The electrode (10) (electrochemically active, i.e. conducting and switchable) is placed on top of a substrate (12), e.g. PET film, i.e. transparency/OH film in one embodiment. The electrode is in one end covered with an electric contact point (17) of an electrically conducting material, e.g. a silver based conductive paint.

Figure 2B:
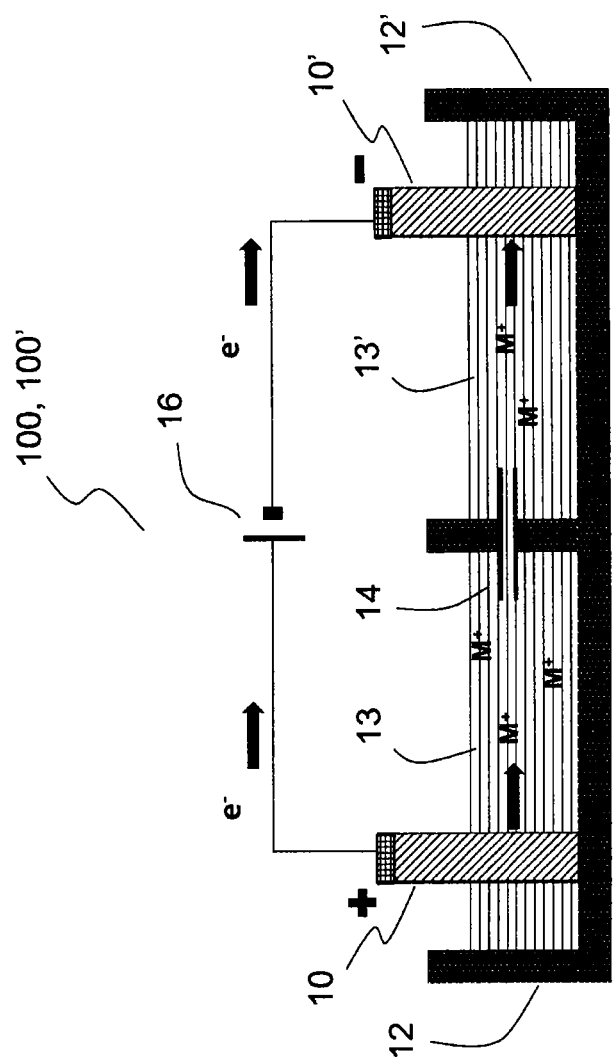

FIG. 2 schematically illustrates two embodiments of an electrokinetic fluid system (100, 100') comprising a first and a second electrode (10, 10') arranged in a respective vessel (12, 12'), an electric potential (16) allowing a controlled flow of electrolyte (13, 13') through a channel (14), one embodiment in FIG. 2A and an alternative embodiment in FIG. 2B.

FIG. 3 schematically illustrates an embodiment of an electrokinetic fluid system 100, such as an electrokinetic separation system 100" according to the present invention. The electrokinetic system comprises two electrodes 10, 10'. The anode 10 and the cathode 10' being connected to an electric potential generating device 16. The electrokinetic system 100 further comprises a first and a second vessel 12, 12', respectively, and at least one capillary element 14 forming a passageway between the first vessel 12 and the second vessel 12'. The first and second vessels 12, 12' comprises an electrolyte 13, 13'. As illustrated, when an electrical potential is applied by means of the electrical potential device 16, a sample to be separated comprised in the electrolyte 13 are transported from the first vessel 12 through the capillary element 14 to the second vessel 12'.

FIG. 4 schematically illustrates an embodiment of a microfludic lab-on-a-chip (LOC) system 200 comprising an electrokinetic fluid system (100) according to the invention. FIG. 4A shows a top view of a substrate (12) material, e.g. a glass microscope slide, corresponding to the vessels in FIGS. 2 and 3. The substrate material is covered with a patterned structure, e.g. patterned cover layer (19) on one side facing the substrate. The patterned structure (19) and substrate (12) create a system of channels and vessels. The patterned cover layer (19) may in one embodiment be made of e.g. of PDMS (polydimethyle siloxane) made by e.g. soft lithography (soft lithography patterned polydimethylsiloxane). Electrodes (10, 10') are fitted into the patterned wholes/cavities/space formed between the patterned cover layer (19) and the substrate (12). Further, a channel (14) is also formed in-between the patterned cover layer and the substrate. The channel is further visualized in the side view FIG. 4B and the end view FIG. 4C.

FIG. 5 shows results in 5A as Absolute (Abs) Current (Ampere), in 5B as Resistance (Ohm), and in 5C as Potenitial (Volt).

Figure 6:
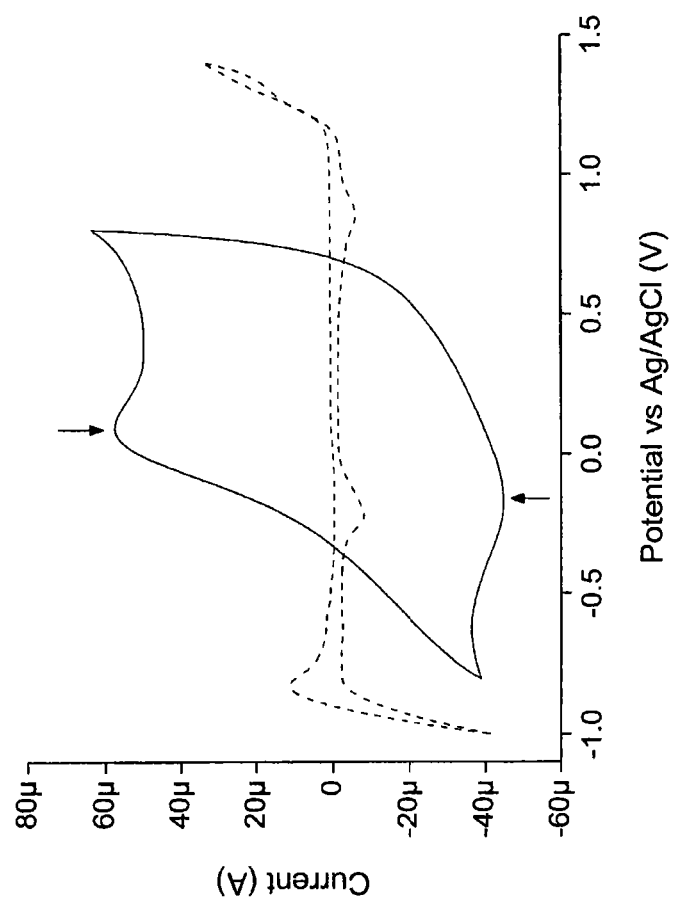

FIG. 6 shows the results in a cyclic voltammogram for platinum (Pt, dotted line) and PEDOT:PSS (solid line) electrodes in 20 mM $NaCL_{(aq)}$. Arrows shows oxidation and reduction peaks associates with PEDOT. E is the applied potential relative an Ag/AgCl electrode.

Figure 7:
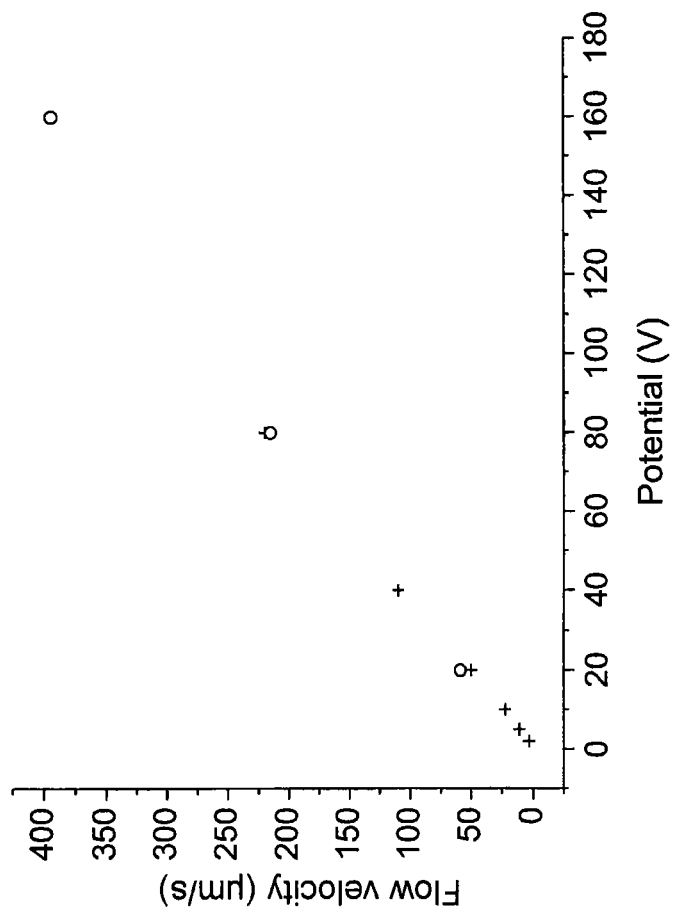

FIG. 7 shows results of flow measurements in 2 individual pumps with a 10 mm-long, 25 μm inner diameter capillary spanning a voltage range of 2V to 160V.

Figure 8:
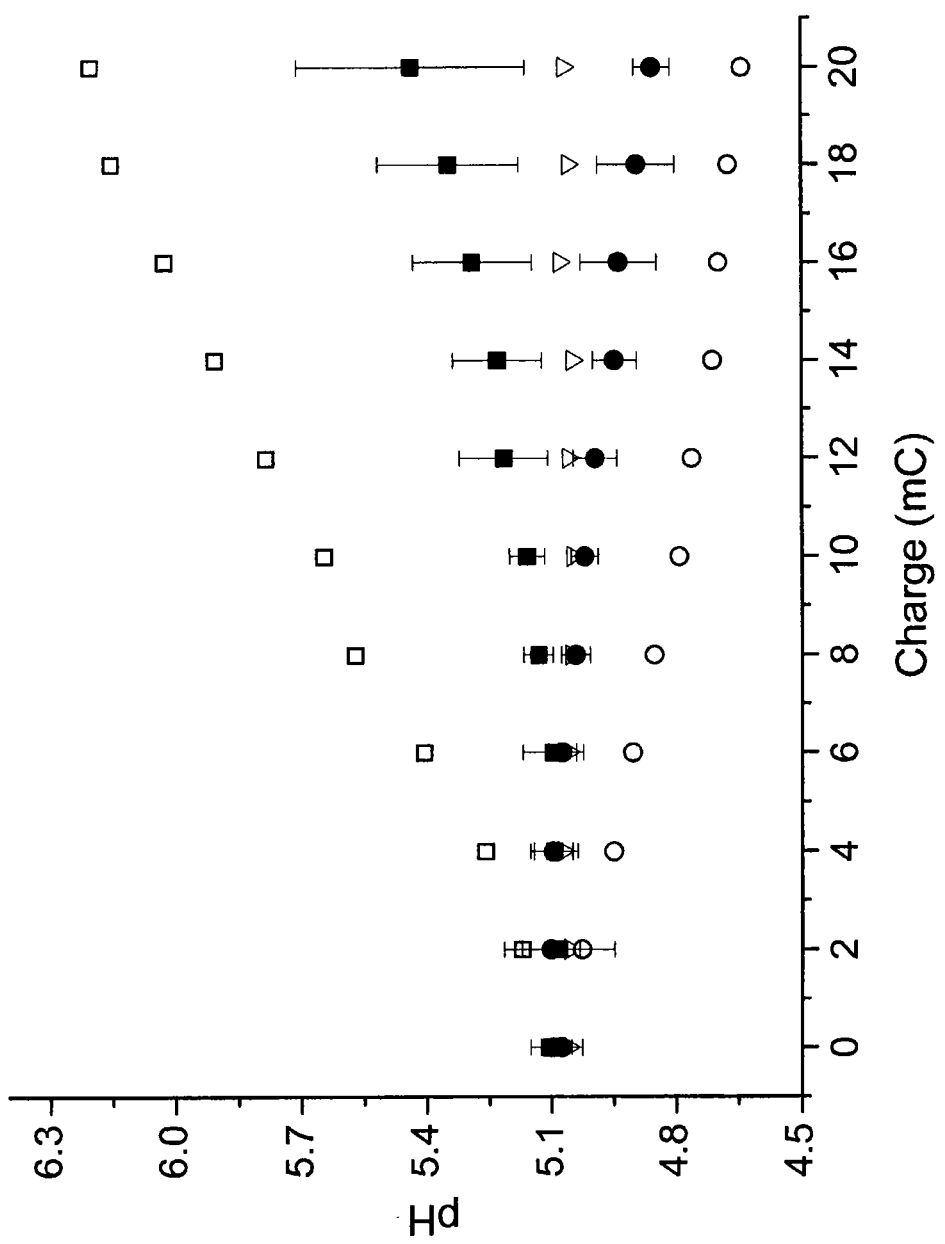

FIG. 8 shows results of pH measurements from two different pumps operated at a constant current of 4 μA. The pump with Pt electrodes shows significant pH changes at both the anode and cathode already when 2-4 mC of charge have been transported. After 10 mC of charge transported, the PEDOT-based pump only shows a pH change of approximately 0.1 pH units. The capacity of the PEDOT electrodes in this experiment was 10 mC, so the polymer electrodes behave similarly to Pt electrodes after that point (pH change increases). Open triangle is control, open circle is anode platinum, open square is cathode platinum, black circle is anode PEDOT, black square is cathode PEDOT. Error bars indicate two standard deviations of the measured data.

Figures 9A, 9B, 9C:
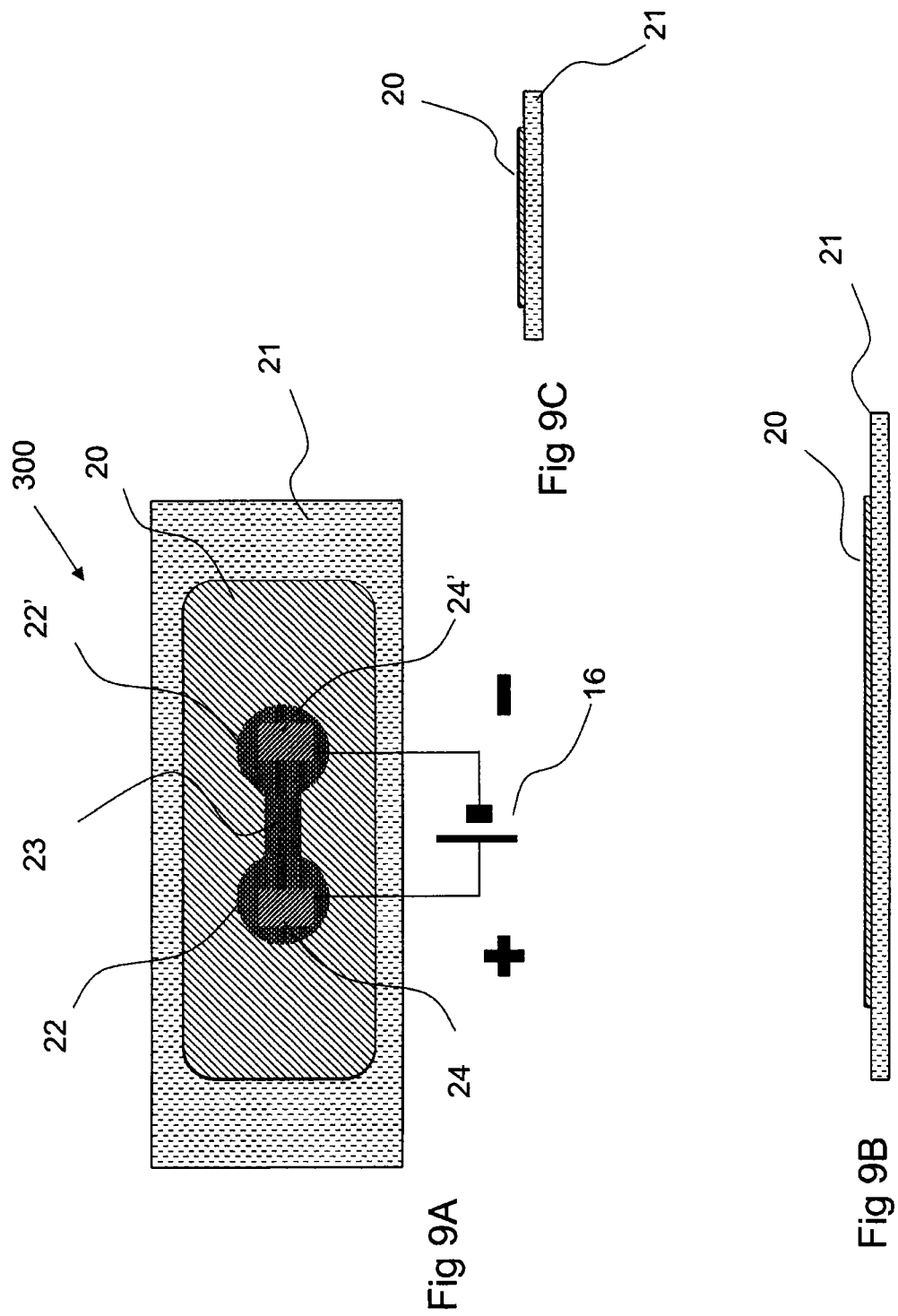

FIG. 9: FIG. 9A shows a top view, FIG. 9B shows a side view, and FIG. 9C shows an end view of a schematic of a combined electroosmotic pump/dielectrophoretic system 300 with pi-conjugated polymer electrodes 24, 24' placed in wells 22, 22' connected by an array of capillaries formed in a PDMS sheet 20, placed on a glass slide 21. Operating the device by using the electric field source 16 to supply a direct current (DC) or alternating current (AC) signal causes flow and/or dielectrophoretic manipulation of particles in the fluid contained in the wells and capillaries.

Figures 10A, 10B:
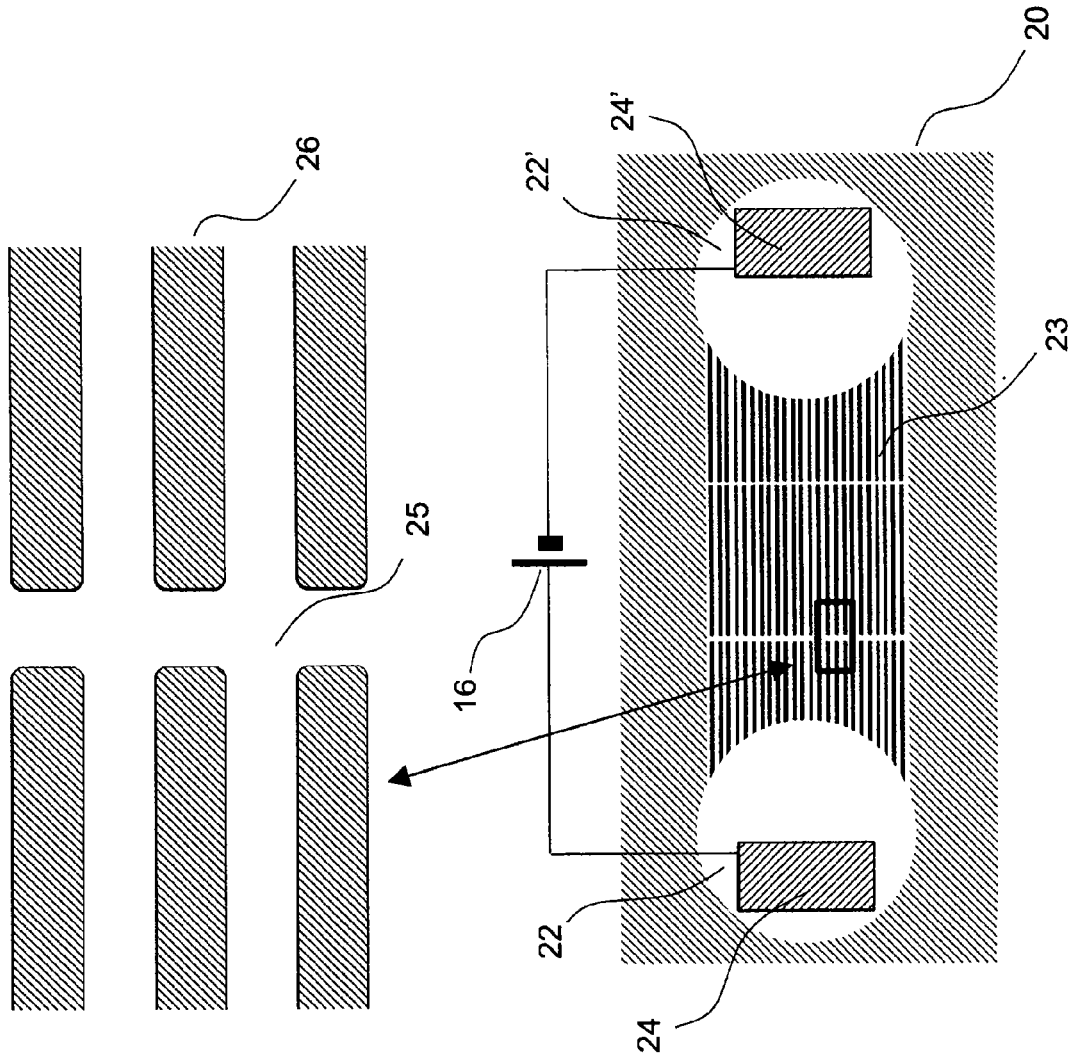

FIG. 10: FIG. 10B shows a close-up of the microfluidic device shown in FIG. 9. FIG. 10A a close-up of the flow channels formed in the PDMS sheet from FIG. 10B. FIG. 10C and FIG. 10D show a photographs of the device in FIG. 9 in operation. In FIG. 10C, a small DC electric field causes the small spherical particles 28 to flow through the channels 25 between PDMS pillars 26. When an AC field is applied, the polystyrene spheres collect and aggregate near the ends of the rectangular structures 26 in the flow area 25, see FIG. 10D.

DETAILED DESCRIPTION OF THE INVENTION

Definitions

As used herein, "electroosmosis" refers to the movement of a liquid inside a capillary, a system of capillaries, a porous plug, a membrane or another micro channel when an electric field is applied.

Further, as used herein, "electrophoresis" refers to the movement of solid particles inside a capillary, a system of capillaries, a porous plug or another micro channel under the influence of an electric field applied relative to the medium in which the solid particles are suspended.

Furthermore, as used herein, "electroosmotic flow" or "EOF" refers to the motion of liquid induced by an electrical field applied across a capillary, a system of capillaries, a porous plug, a membrane or another micro channel.

As used herein, "electrochemically active material" refers to a material which may comprise a proportion of a component in an electrochemical reaction when it is in contact with an electrolyte and an electric current is allowed to flow to or from it. Examples of such electrochemically active materials include electrically conductive polymers, as will be described below, carbon and certain metal oxides, e.g. manganese dioxide ($MnO_2$) and tungsten oxide ($WO_3$). Said electrochemically active material can be electrochemically oxidized or reduced, i.e. its oxidation state can be changed via electrochemistry.

As used herein, "liquid" is intended to mean one of the three classical states of matter, which, together with gas shares the ability to flow. Like a gas, a liquid is able to flow and take the shape of a container, but, like a solid, it resists compression. Unlike a gas, a liquid does not disperse to fill every space of a container, and maintains a fairly constant density. A liquid is a fluid. Unlike a solid, the molecules in a liquid have a much greater freedom to move. The forces that bind the molecules together in a solid are only temporary in a liquid, allowing a liquid to flow while a solid remains rigid.

As used herein, the term electrolyte for use with the system, methods and uses of the present invention should preferably be based on a liquid which permits ionic conduction in the electrolyte, i.e. which allows for the dissociation of ionic substances such as salts, acids, bases etc. The liquid and/or the ionic substance may contribute nucleophiles. Possible electrolytes for use in combination with the inventive system are solutions/liquids of salts, acids, bases, or other ion-releasing agents in solvents that support the dissociation of ionic species, thus allowing ionic conductivity. In applications where it is required, the electrolytes may comprise buffer solutions, such as buffer solutions suitable for use with living organisms or biomolecules, such as proteins. Examples of such buffers suitable for use with living organsisms or biomolecules include NaHPO4 and sodium acetate. As other non-limiting examples of possible electrolytes, mention can be made of: aqueous solutions of potassium acetate, calcium acetate, NaCl, Na2SO, HCl, H3PO4, HaSO4, KCl, RbNO3, NH4OH, CsOH, NaOH, KOH, H2O2; Ringer's solution, organic solvents such as acetonitrile, pyridine, DMSO, DMF, dichloromethane, etc., in combination with suitable salts, such as sodiumperchlorate or sodiumtrifluoromethylsulfonate and tertiary ammonium salts, e.g. tetra-butyl ammonium chloride; inorganic solvents such as hypercritical $CO_2$, liquid $SO_2$, liquid $NH_3$, etc., in combination with salts that dissociate in these solvents/liquids; solvents/liquids displaying autodissociation, which results in the formation of ionic species, such as water, formic acid and acetic acid. The term electrolyte also encompasses solutions comprising charged biologically active molecules or macromolecules such as charged amino acids, DNA, DNA fragments and plasmids, proteins, vitamins, peptides or hormones. An electrolyte may also comprise cell culturing media or ingredients thereof, such as proteins, amino acids, vitamins, and growth factors.

The term electrolyte may also encompass solutions comprising charged aggregate particles such as emulsified species, or species clad with some additional charged species. An example of such electrolytes include milk, urine and blood.

As used herein, "microfluidics" deals with the behavior, precise control and manipulation of fluids that are geometrically constrained to a small, typically sub-millimeter, scale.

A "microfluidic device" is a device that employs sub-millimeter scale channels, or pores. This could be for use with small volumes of fluid (e.g. LOC techniques), or because the desired physics is only applicable at these small length scales (such as electroosmotic flow generated in an electroosmotic pump).

As used herein a "lab-on-a-chip" or "LOC" is intended to mean a device that integrates one or several laboratory functions on a single chip of only a few square millimeters to a few square centimeters in size. LOCs deal with the handling of extremely small fluid volumes down to less than pico liters. Lab-on-a-chip devices are a subset of MEMS devices (Micro-electromechanical systems, MEMS) and often indicated by "Micro Total Analysis Systems" (µTAS) as well." Microfluidics is a broader term that describes also mechanical flow control devices like pumps and valves or sensors like flowmeters and viscometers. However, "Lab-on-a-Chip" usually indicates generally the scaling of single or multiple lab processes down to chip-format, whereas "µTAS" is dedicated to the integration of the total sequence of lab processes to perform chemical analysis. The term "Lab-on-a-Chip" has been introduced later in time when it turned out that µTAS technologies were more widely applicable than only for analysis purposes.

As used herein, the term "semi-solid material" is intended to mean a material, which at the temperatures at which it is used has a rigidity and viscosity intermediate between a solid and a liquid. Thus, the material is sufficiently rigid such that it does not flow or leak.

As used herein, "species" is intended to mean an ion, a molecule, charged or not, or any particle or biological sample as exemplified herein or known in the art, such as a protein, DNA, RNA, microRNA, interleukin, hormone, signaling substance such as neurotransmitters, hormones and ions etc. Further examples are given herein.

As used herein, the term "cell" is meant to encompass all types of animal or plant cells that may be of interest to cell studies.

Non limiting examples of types of cells that may be used with the present invention include eukaryotic cells which are cells with nucleus and prokaryotes which are cells without nucleus.

Non limiting examples of eukaryotic cells include stem cells and nerve cells, cells from the immune system, epithelial cells, and endothelial cells. Non limiting examples of prokaryotic cells include different kinds of bacteria. A person skilled in the art of cellular research would readily be able to name any number of different cells that may be used with the present disclosure.

Cell sizes of cells useful with the present invention are typically in the range of 1 µm-1 mm and may for example be in the range of 10-500 µm in diameter or in the range of 10-100 µm or 10-50 µm. Also some types of cells that may be of interest will be straggling.

Further, a cluster of cells are encompassed. As the term is used in the present disclosure, is meant a number of adjacent cells ranging from 2 cells to millions of cells. Typically a cluster of cells may comprise about 2-1 000 000 cells, for example about 100 000-1 000 000 cells. One specific example of a cluster of cells would comprise a slice, such as an explant, or a small portion of a slice of tissue from an organ or neurons that would be of interest to study using a device according to the present disclosure. A person skilled in the art of cellular research would readily be able to name other types of cell clusters that may be of interest to study using a device according to the present disclosure.

While the invention covers various modifications and alternative methods, apparatuses and systems, embodiments of the present invention are shown in the drawings and will hereinafter be described in detail. However, it should be understood that the specific description and drawings are not intended to limit the scope of the claims invention to the specific forms disclosed. On the contrary, the scope of the claimed invention is intended to include all modifications and alterative constructions thereof falling within the spirit and scope of the invention as expressed in the appended claims to the full range of the equivalents. In the drawings, the same reference numerals are used to indicate the same or similar features.

Thus, one object of the present invention is to provide an electrokinetic fluidic system (100, 100', 100") for controlling liquid flow, characterized in that it comprises
  a) a first and a second electrode (10, 10') arranged in a respective vessel (12, 12'), said electrodes comprise a polymer based or oxide based conductive, electrochemically active electrode material, said electrode material being adapted to be subjected to an electrochemical reaction when in use in said electrokinetic fluid system (100), and wherein the conductive, electrochemically active electrode material is selected from the group of pi-conjugated polymers.
  b) a channel (14) arranged as a passageway between the two vessels, said channel allowing flow of electrolyte (13, 13') between said two vessels (12, 12').

Said channel arranged as a passageway may be any type of channel connecting the two vessels, such as one or more tunnels or holes like one or more channels or one or more tubes. Further examples are one or more capillary elements or any porous material that may or may not be in a tube like or channel like form or area. The channel may be short or long. In a short form, the channel is more of a hole or membrane, however, enough to allow a flow of liquid such as an electrolyte (13, 13').

The electrokinetic fluidic system (100, 100', 100") according to the invention may further be arranged so that the electrode material is arranged at least at a surface of said electrode (10,10'), said surface being facing an electrolyte (13,13') when the electrode (10,10') is in use in said electrokinetic fluid system (100).

The electrokinetic fluidic system (100, 100', 100") according to the invention may further be characterized in that the conductive, electrochemically active electrode material conducts electricity in at least one reduction-oxidation state, is electrochemical switchable, does not break apart and does not release toxic substances or other substances that could alter or damage a chemical or biological sample into the electrolyte (13,13').

A toxic substance is measured by its toxicity. Toxicity is the degree to which a substance is able to damage an exposed organism. Toxicity can refer to the effect on a whole organism, such as an animal, bacterium, or plant, as well as the effect on a substructure of the organism, such as a cell (cytotoxicity) or an organ (organotoxicity), such as the liver (hepatotoxicity). A central concept of toxicology is that effects are dose-dependent; even water can lead to water intoxication when taken in large enough doses, whereas for even a very toxic substance such as snake venom or a metal ion such as cupper there is a dose below which there is no detectable toxic effect. There are generally three types of toxic entities; chemical, biological and physical. Chemical include inorganic substances such as lead, mercury, asbestos, hydrofluoric acid, and chlorine gas, organic compounds such as methyl alcohol, most medications, and poisons from living things.

Toxicity of chemicals can be measured by the effects on the target (organism, organ, tissue or cell). Because individuals typically have different levels of response to the same dose of a toxin, a population-level measure of toxicity is often used which relates the probabilities of an outcome for a given individual in a population. One such measure is the $LD_{50}$. When such data does not exist, estimates are made by comparison to known similar toxic things, or to similar exposures in similar organisms.

Thus, the system of the invention (100, 100', 100") is a system where no toxic substances or chemicals are released into the electrolyte. Toxicity may also be evaluated in a cell based or cell free system, such as a cell culture or a lysed cell system, wherein a toxic substance may affect or hamper e.g. activity of an enzyme, cell metabolism, cell growth and proliferation, cell survival etc.

Thus, said system of the invention allows for a "safe" environment in the system of the invention. Biological samples are highly sensitive for changes in pH, ions and metals, such as metal ions in solution and the system of the invention allows for a bubble fee environment with a stable pH, since the electrolyte is not consumed.

The electrokinetic fluidic system (100, 100', 100") according to the invention is characterized in that the conductive, electrochemically active electrode material is selected from the group of pi-conjugated polymers.

Examples of suitable conductive polymers are pi-conjugated polymers. Thus, the conductive, electrochemically active electrode material may comprise any conductive, electrochemically active electrode material selected from the group consisting of polyacetylenes, polypyrroles, polythiophenes, polyanilines, poly(p-phenylene sulfide), poly(p-phenylene vinylene)s, polyindole, polypyrene, polycarbazole, polyazulene, polyazepine, polyfluorenes, polynaphthalene and polyisothianaphthalenes, a copolymer thereof, or a mixture thereof.

Thus, in further embodiments, the electrokinetic fluidic system (100, 100', 100") according to the invention is characterized in that the conductive, electrochemically active electrode material comprises any of a
polyacetylenes, polypyrroles, polythiophenes, polyanilines, poly(p-phenylene sulfide), poly(p-phenylene vinylene)s, polyindole, polypyrene, polycarbazole, polyazulene, polyazepine, polyfluorenes, polynaphthalene and polyisothianaphthalenes, a copolymer thereof, or a mixture thereof.

One example of a mixture or blend is where the electrode comprises a blend of poly(3,4-ethylenedioxythiophene) and poly(styrenesulfonate) abbreviated as PEDOT:PSS.

By coating a metal electrode with a pi-conjugated polymer or using the pi-conjugated polymer itself as the electrode, the electrochemistry at the electrodes can be induced at almost any potential and pumping starts at very low voltages. For example, if Pt electrodes were used and electrolysis of water provided the Faradaic reaction, then at least 1.2 (and probably 2-3) V would need to be provided before significant pumping occurred because electrolysis does not occur below these potentials. However, if a pi-conjugated polymer, such as e.g. PEDOT:PSS, starting e.g. in a partially-doped state (as cast from solution) is used instead of Pt or on top of the Pt, it begins being oxidized or reduced already at mV potentials. In other words, electrochemistry (and hence flow) can be driven at potentials lower than those required for performing electrolysis on the solvent. This is particularly useful for hand-held microfluidic devices that may be driven by a battery or, e.g. a 5V supply via a computer USB port or cell phone.

The system described herein may further be used at high voltages, several hundred volts, over e.g. a capillary to induce a field of 100V/cm or more to be able to transport a fluid at a speed of effectively 400 µm/s or more. The system of the invention as described herein thus works both at high, i.e. greater than one hundred volts, and low, i.e. 2 volts or lower, voltage.

The conductive, electrochemically active electrode material may also comprise a metal oxide. Examples are e.g. vanadium oxide or tungsten oxide Further embodiments are wherein the electrokinetic fluidic system (100, 100', 100") according to the invention is characterized in that the conductive, electrochemically active electrode material comprises a metal oxide, such as a e.g. vanadium oxide or tungsten oxide.

The fluidic system (100, 100', 100") according to the invention comprises a channel (14). Said channel (14) may be at least one capillary element allowing flow of electrolyte (13, 13'). At least one means 1, 2, 3, 4, 5, 6, 7, 8, 9, 10, 20, 30, 40, 50, 60, 70, 80, 90 or even 100 capillary elements, such as 100, 200, 300, 400, 500, 600, 700, 800, 900 or even 1000 capillary elements together.

Said channel (14) may be a network of capillaries, such as the one shown in FIG. 9, used to demonstrate the device with dielectrophoretic manipulation of polystyrene beads as shown in FIG. 10.

Said channel (14) may be a porous material such as fritted glass, a polymer monolith, a membrane, or a vessel packed with particles such as silica beads. The porous material may be a bead or similar structure. Porous materials are classified into several kinds by their size. According to IUPAC notation (J. Rouquerol et al. (1994). "Recommendations for the characterization of porous solids (Technical Report)" *Pure & Appl. Chem* 66: 1739-1758, see http://www.iupac.org/publications/pac/66/8/1739/pdf/) microporous materials have pore diameters of less than 2 nm and macroporous materials have pore diameters of greater than 50 nm. A mesoporous material is a material containing pores with diameters between 2 and 50 nm.

Thus, said porous material may be a microporous material or a macroporous material. Still even further said porous material may be a mesoporous material.

Said channel (14) may further be a porous material of solid or semi-solid material allowing flow of electrolyte liquid (13, 13').

Said channel (14) may be formed by any appropriate matrix material, such as a paper, a fabric or a porous polymer, e.g. in the form of a channel or in the form of a membrane.

Suitable electrolytes are known in the art and further exemplified herein. It also includes so called ionic liquids, which are liquids that contain essentially only ions. Examples of these are quarterial ammonium salts, phosphonium salts, mixtures of 1,3-dialkylimidazolium or 1-alkylpyridinium halides and trihalogenoaluminates, EMIM EtOSO3 (1-Ethyl-3-methylimidazolium ethylsulfate), $LiClO_4$ dissolved in 1-butyl-3-methylimidazolium tetrafluoroborate.

Said channel may be formed of a polycation, such as protonated poly-L-lysine or a polyanion such as polymers containing sulfonate groups such as poly(styrenesulfonate).

Further, the walls of said channel may be charged, often via the dissociation of a salt or deprotonation of an alcohol group. For example, the silanol on silicon oxides often deprotonates, leaving a negatively charged oxygen atom at the surface. Salts of polyanions such as sodium poly(styrenesulfonate) disso-ciate, leaving the immobile sulfonate ion at the surface. Another example is the protonation of poly-L-lysine at appropriate pH values, causing the stationary interface to have a net positive charge.

Further, said channel may be about ≤200 µm in diameter, such as e.g. 200, 150, 100, 75, 50, 25, 10, 5, 2, 1, µm, or even 900, 800, 700, 600, 500, 400, 300, 200, 100, 50, 25, 10, 5, 2, 1 nm in diameter.

Further, the electrokinetic fluidic system (100, 100', 100") according to the invention may further comprises an electric potential/field generating device (16).

Examples of electric potential/field generating devices (16) are batteries, source-measure units, or other power supplies such as those providing a voltage or a current to the system of the invention. Said power supply can be directly attached to the LOC system substrate, e.g. as a battery, or can be part of a separate system, e.g. as a power supply, connected via conducting contacts.

Magnitude and polarity of the voltages to be applied in the inventive system, kits and methods will vary depending on a number of factors, such as choice of electrode material(s), the ion to be transported, the distance over which the ions are transported, the desired transport rate, etc. The polarity of the applied voltages will easily be selected by a person skilled in the art, taking into account the type of charge (positive or negative) of the ion to be used to drive EOF or to be separated via electrophoresis. The magnitude of the voltage to be applied may in the light of the present invention easily be determined in order to transport a desired rate or amount of fluid or to optimize a separation.

The voltage applied across the system including its channel may for example be within the range of from about 0.01V to about 100 V. The optimal voltage to apply between electrodes will thus depend on the characteristics of the channel, the electrolyte used, the electrolyte to be transported and the manner in which the voltage is applied to the electrodes.

However, the voltage is preferably in the range of from 0.01 to 100 V, more preferably in the range of from 0.01 V to 20 V.

One further highly desirable and unexpected effect achieved in the system of the invention is that when a pi-conjugated polymer is used, the pumping in said system may start at in principle any voltage, for example a very low voltage. A low voltage is beneficial for biological samples, and for devices to be powered by batteries, solar cells and other low-voltage power sources, particularly small, portable devices.

FIG. 2 schematically illustrates an embodiment of the electrokinetic fluidic system (100) according to the invention.

As illustrated in FIG. 2 the electrokinetic fluidic system (100, 100', 100") comprises a first and a second electrode (10, 10') arranged on a respective substrate, here, as in a vessel (12, 12'), and an electric field (16) allowing a controlled flow of electrolyte (13, 13') through a channel (14).

Said substrate is in FIG. 2 shown as a vessel and in FIG. 1 as a mere substrate for sticking the electrode onto, may be made of a OH-film, e.g. a transparent OH-film, such as a PET-film/transparency film.

In FIG. 1, the electrode is in one end covered with an electric contact point (17) of an electrically conducting material, e.g. in one embodiment being a conductive silver paint.

The electrode may comprise a conductive, electrochemically active material such as a conductive polymer or a conductive metal oxide, or a combination thereof, e.g. a composite or a co-polymer. Examples of conductive polymers are given herein. Further, also a "thick" i.e. 250 nm or thicker layer of the material may be placed on a metal, e.g. Au (gold), electrode as long as the e.g. polymer covers the metal so that hydrolysis does not occur there. Preferably, at least the outermost layer/surface, i.e. the layer/surface which is in contact with the electrolyte during operation, of the electrode should consist essentially of the conductive, electrochemically active material.

It is also possible to use a combination of two or more materials where at least one of the materials is electrically conductive and at least one of the materials is capable of conducting ions. Examples of such combinations, which may be used in a system according to the present invention, include an electrically conductive material, such as indium tin oxide, and an ion-conductive hydrogel.

The electrodes may also comprise further organic or inorganic materials, which are capable of conducting ions but not capable of conducting electrons, which materials are included in order to facilitate ion transport into and within the electrodes. Non-limiting examples of such materials are polymer materials, such as hydrogels and polyelectrolytes. Such additional electrode materials may be either dispersed in, or be arranged as a separate layer in contact with, an electrically conductive electrode material.

The electrodes of the system according to the invention preferably comprise an electrochemically active material. Said electrode material may be an organic material. Said organic material may be a polymer, and may be an electrically conductive polymer.

Electrically conductive polymers suitable for use in the system of the invention, are preferably selected from the group consisting of polyacetylenes, polypyrroles, polythiophenes, polyanilines, poly(p-phenylene sulfide), poly(p-phenylene vinylene)s, polyindole, polypyrene, polycarbazole, polyazulene, polyazepine, polyfluorenes, polynaphthalene and polyisothianaphthalenes, a copolymer thereof, or a mixture thereof such as described by J C Gustafsson et al. in Solid State Ionics, 69, 145-152 (1994); Handbook of Oligo- and Polythiophenes, Ch 10.8, Ed D Fichou, Wiley-VCH, Weinhem (1999); by P Schottland et al. in Macromolecules, 33, 7051-7061 (2000); by M Onoda in Journal of the Electrochemical Society, 141, 338-341 (1994); by M Chandrasekar in Conducting Polymers, Fundamentals and Applications, a Practical Approach, Kluwer Academic Publishers, Boston (1999); and by A J Epstein et al. in Macromol Chem, Macromol Symp, 5 1, 217-234 (1991).

In further embodiments, the electrically conductive polymer is a polymer or copolymer of a 3,4-dialkoxythiophene, in which said two alkoxy groups may be the same or different or together represent an optionally substituted oxy-alkylene-oxy bridge. The polymer may be a polymer or copolymer of a 3,4-dialkoxythiophene selected from the group consisting of poly(3,4-methyleneioxythiophene), poly(3,4-methylenedioxythiophene) derivatives, poly(3,4-ethylenedioxythiophene), poly(3,4-ethylenedioxythiophene) derivatives, poly(3,4-propylenedioxythiophene), poly(3,4-propylenedioxythiophene) derivatives, poly(3,4-butylenedioxythiophene), poly(3,4-butylenedioxythiophene) derivatives, and copolymers therewith.

In one embodiment of the system, said electrically conductive polymer is poly(3,4-ethylenedioxythiophene) (PEDOT). The electrodes may further comprise a polyelectrolyte compound, e.g. poly(styrene sulfonic acid) or a salt thereof. One example of a material for use in the electrodes of the device of the invention is poly(3,4-ethylenedioxythiophene) with a poly(styrene sulfonate) polyanion (in the following referred to as PEDOT:PSS). In an embodiment the electrodes are present in the form of a thin layer of PEDOT:PSS deposited on a solid substrate.

The electrodes of the inventive device may further comprise a hydrogel. The hydrogel is preferably based on polymers selected from the group consisting of polyacrylates, such as poly(2-hydroxyethyl methacrylate) and poly(acrylamide), polyelectrolytes, such as poly(styrene sulfonic acid) (PSS) and poly(acrylic acid) (PAA), polysaccharides, such as agarose, chitosan and dextran, gelatin, polyvinyl alcohol, polyvinyl pyrrolidone, polyethylene oxide and polyethylene glycol.

The electrodes may further be present in the form of a thin layer of PEDOT:PSS deposited on a solid substrate and a thin layer of chitosan deposited on said PEDOT:PSS layer. Other combinations of materials can also be used.

The electrode material conducts electricity in at least one reduction-oxidation state, may be electrochemically switchable between 2 or more redox states, usually a blend of e.g. oxidized and neutral material, does not break apart and does not release toxic substances into the electrolyte. Further, if a blend, the concentrations of the oxidized and neutral material may change as electrochemistry occurs. Further embodiments are wherein the material is non-conductive in its neutral state, e.g. poly(3-hexylthiophene).

By electrochemically switchable is, in this description, meant that the electrode material should be able to change oxidation state upon switching the applied electric potential to the electrode relative to the opposite electrode and/or electrolyte in the electrochemical system. The material must be able to incorporate or release cations or anions from the electrolyte to create or maintain the electric field in the electrolyte without itself breaking down and/or releasing toxic material or material that would otherwise interfere with the sample being transported.

The materials can be deposited in various oxidation states. The state may then be modified via redox chemistry or electrochemistry after it is deposited.

The materials may undergo reversible electrochemical reactions, so that the anode can become the cathode and vice versa simply by reversing the polarity of the potential applied between the electrodes. Further one or both electrodes may undergo an irreversible reaction, so that the device cannot be reversed.

Examples of suitable conductive metal oxides are vanadium oxide, and tungsten oxide.

The conductive, electrochemically active material, e.g. PEDOT:PSS, can be readily coated or printed e.g. using ink-jet, screen, or other printing technologies, on a substrate, thereby forming an electrode. When the conductive, electrochemically active material is a metal oxide, it could also be applied to the substrate by other conventional methods, for example by means of a sol-gel process, physical vapor deposition (PVD) or chemical vapor deposition (CVD). The substrate could for example be plastic like polyethylene terephthalate (PET) or polystyrene, or a glass such as silica or quartz.

However, it should be understood that the entire electrode could be manufactured of the conductive, electrochemically active material or of a combination of conductive, electrochemically active materials, for example in the form of a layered product or a composite.

By using a conductive, electrochemically active material, e.g. PEDOT:PSS, as electrode material in an electrokinetic fluid system, the impact on the pH of the electrolyte during reduction-oxidation reactions is minimized as compared to electrokinetic fluid systems wherein a metal is used as electrode material. Thus, by using electrodes comprising PEDOT:

PSS, the pH of the electrolyte will remain the same, i.e. constant or almost constant, during reduction-oxidation reactions.

Further, the PEDOT:PSS as electrode material will limit buffer depletion, i.e. pH consumption, and decrease the risk of bubbles forming inside the electrokinetic fluid system. Furthermore, the association of ions which compensate for reduction-oxidation reactions in the PEDOT:PSS is non-specific and allows the electrodes to be used in any electrolyte used today in LOCs.

The electrode may further be configured to mate the inner surface of a vessel at which inner surface the electrode is to be arranged with or without any space there between. As schematically illustrated in FIG. 2, the electrodes 10,10' may mate the inner surface at both the side walls and the bottom of the vessels 12,12' or may be as shown in FIG. 3, with a short distance between the substrate vessel and the electrodes. The figure illustrates a laboratory-scale capillary electrophoresis setup.

However, it should be understood that the electrode could have other shapes such as cylindrical, cubical, or spherical and further, that the dimensions, e.g. the width, length, and thickness, of the electrode may vary as such depending on the specific application. The electrodes may be arranged in a common plane on a solid substrate. In some embodiments, the electrodes are deposited onto said substrate by printing or lamination techniques. Use of printing methods in combination with conventional semiconductor processing methods, such as lithography and etching, allows for the electrodes to be patterned with a resolution of about 1 μm. This allows the inventive device to be manufactured in miniature scale, which e.g. is useful in biochemical and cell applications where samples and preparations may be available only in very minute amounts.

In further embodiments, the thickness of the electrodes is less than 1 mm. The thickness is measured in a direction normal to the support on which the electrode is arranged.

Further in the system provided, at least one of the electrodes may be biocompatible. The term biocompatible is used herein to characterize a material or a surface allowing cultivation of cells thereon or in close association therewith. Cultivation of cells refers to attachment, maintenance, growth and/or proliferation of said cells. An example of an electrode material according to the invention that provides a biocompatible surface is PEDOT:PSS. The biocompatibility of an electrode allow for studies of cellular activities in cells cultivated on or in close association with the electrode.

A cell contact site may be realized by means of one or more physical or chemical confinement methods. The cell(s) may for example be confined by walls or the like arranged on the device surface, by openings in a partial encapsulation of the system as described herein, or by suitable chemical or physical treatment of the system surface.

The cell(s) may be retained on the system by means of a container, arranged such that the cell(s) are in contact with the desired electrodes. Said container may preferably be made of glass or a polymer material, but other materials may also be used. The container may be open or partly or fully sealed. In an embodiment of the invention, said system comprises a multiplicity of said single arrangements and their related cell contact sites, the system and their related cell contact sites preferably being arranged to create a matrix system thereof, wherein each system may be addressed individually for charged or non-charged species, such as molecules and ions, transport purposes. An example of an application where such a matrix system would be useful is in microwell plates, as used e.g. for cell culturing and biochemical research. Management of such a matrix system could conveniently be handled by a personal computer.

In the inventive apparatus or system (100, 100', 100"), each system and its related cell contact site is arranged to provide ionic contact between a single cell and the target or source electrolyte, respectively. Such single cell contact is rendered possible by the small dimensions achievable in the production of the inventive system. Thus, according to the present invention it is possible to address a single cell, or even specific portions of a single cell to, or from, which ions or charged or non-charged species, such as molecules and ions, are being transported.

As previously mentioned, the conductive, electrochemically active material, could be applied to a substrate to form the electrode. In such embodiments, the applied layer of conductive, electrochemically active material may have a thickness in the range that is suitable for the specific application. There is no limited range of thickness in which the electrode will operate.

FIG. 2 schematically illustrates an embodiment of an electrokinetic fluid system 100, such as an electrokinetic pumping system 100', e.g. an electroosmotic pump, according to the present invention. The electrokinetic system 100, 100' comprises two electrodes 10, 10'. The anode 10 and the cathode 10' being connected to an electric field generating device 16. The electrokinetic system 100 further comprises a first and a second vessel 12, 12', respectively, and at least one duct or channel or through hole 14 forming a passageway between the first vessel 12 and the second vessel 12'. The first and second vessels 12, 12' comprises an electrolyte 13, 13', e.g. an aqueous liquid or an organic liquid or a mixture thereof. As illustrated, when an electrical field is applied by means of the electrical field device 16, metal cations $M^+$, such as $Na^+$, comprised in the electrolyte 13 are transported from the first vessel 12 through the channel 14 to the second vessel 12'.

Further, referring to the embodiment in FIG. 2, due to the applied electrical field electrochemical reactions occur at the anode 10 and cathode 10', respectively. At the anode 10, the electrode material may be e.g. PEDOT:PSS in an undoped state is changed to a p-doped state, indicated as $P^+$, at the same time as an ion $M^+$ is released from the electrode material. Further, at the cathode 10', an ion $M^+$ enters the electrode material and the electrode material PEDOT:PSS in a p-doped state e.g. $P^+$, is changed to an un-doped state indicated as $P^0$. This is an oxidation of neutral PEDOT ($P^0$) to oxidized PEDOT ($P^+$).

The reactions are exemplified in

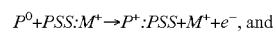

$P^0 + PSS{:}M^+ \rightarrow P^+{:}PSS + M^+ + e^-$, and

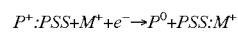

$P^+{:}PSS + M^+ + e^- \rightarrow P^0 + PSS{:}M^+$

A PEDOT chain can be oxidized many times since it is so long. PEDOT is always synthesized in a partially (nearly fully) doped/oxidized state. Most other polymers are produced in the neutral state. They all can be oxidized/reduced in-situ before use. In the case of a PEDOT:PSS blend, the PSS is always present and always negatively charged. When PEDOT is doped (positively charged), it uses the PSS as a counter-ion to balance the charge. When PEDOT is neutral, the PSS needs another ion (e.g. $Na^+$) to balance the charge. The second reaction is the reverse process (reduction of doped PEDOT to neutral PEDOT).

Note that other materials, such as P3HT, don't have PSS, and therefore typically require an anion when positively charged (doped). The general principle is the same.

One important characteristic of a suitable electrode material is that the electrochemical change in the electrode's reduction-oxidation state occurs within the electrochemical stability window of the electrolyte, e.g. water, and that the electrode material remains within the electrode rather than being released into the electrolyte.

An electrochemical stability window is defined as the potential range in which an electrode can be polarized in a solution without the passage of Farradic currents. The electrochemical stability window of electrolyte-solution systems depends on the i) nature of the solvent, ii) nature of the salt, iii) nature of electrode materials, and iv) presence of contaminants. It depends on the inherent electrochemical stability of its individual components.

Methods

Further objects of the present invention is to provide a method to control liquid flow, of e.g. an electrolyte, in an electrokinetic fluidic system, the method comprising
  a. applying an electric field to a first and a second electrode (10, 10') arranged in a respective vessel (12, 12'), said electrodes comprise a polymer based or oxide based conductive, electrochemically active electrode material, said electrode material being adapted to be subjected to an electrochemical reaction when in use in said electrokinetic fluid system (100, 100', 100"),
  b. controlling said electric field by means of an electric field device (16), allowing a controlled flow of electrolyte (13, 13').

Further, the electrokinetic fluidic system is, of course, according to any electrokinetic fluidic systems of the present invention.

Further, said method may comprise the steps of controlling flow of charged species in said electrolyte. Said control of flow is achieved using the system of the present invention.

The method may further comprises the steps of controlling flow of non-charged species in said liquid electrolyte or wherein the electrolyte flows and with it carries non-charged species.

Said flow of charged and non-charged species in said electrolyte (13, 13') may be controlled by controlling said electric field by means of an electric field device (16), allowing a controlled flow of electrolyte (13, 13') using a system according to the invention, e.g. as described in FIG. 2.

Further objects are to provide a method allowing controlled flow of charged and non-charged species in an electrokinetic fluidic system, the method comprising
  a. providing a charged or non-charged species on the electrolyte (13, 13') in a first or a second vessel (12, 12'),
  b. applying an electric field to a first and a second electrode (10, 10') arranged in a respective vessel (12, 12'), said electrodes comprise a polymer based or oxide based conductive, electrochemically active electrode material, said electrode material being adapted to be subjected to an electrochemical reaction when in use in said electrokinetic fluid system (100, 100', 100"),
  c. controlling said electric field by means of an electric field device (16), allowing a controlled flow of electrolyte (13, 13'), thereby allowing a controlled flow of a charged or non-charged species in said electrolyte (13, 13').

Examples of charged species are mono and divalent metal cations such as $Na^+$, $Ca^{2+}$ and $K^+$, charged anions such as $Cl^-$, $F^-$, $SO_3^-$, charged biological species such as proteins, amino acids, peptides and nucleic acids.

Examples of non-charged species include sugars, fats, uncharged peptides, amino acids with a net zero charge (at a certain pH) and proteins with a net zero charge (at a certain pH), biologically interesting species such as hormones (estrogen, progesterone, etc.) Even large species with a small charge relative to their mass can behave as uncharged species in an electrokinetic system, since their mobility is so small. Similarly, charged and non-charged particles (microparticles, nanoparticles), droplets, or bubbles suspended in a liquid can be transported.

System

Further objects are to provide a systems such as LOC (200) or combinations with dielektrophoresis (DEP) systems (300) for manipulating, transporting, and/or separating bubbles, cells or particles such as nanoparticles, nanotubes, or beads, comprising an electrokinetic fluid system (100, 100', 100") according to any part of the invention.

Further, the system herein (100, 100', 100", 200, 300) may include a microfluidic channel with a change in inner dimension such as a constriction or expansion, or containing objects such as pillars or columns, possibly in an array (as shown in FIG. 10) forming a network, patterned in a material such as PDMS or glass or both (e.g. the walls and ceiling of the channel/network are PDMS while the floor is glass). When the channel/network is filled with a fluid and an electric field is generated by applying a potential between electrodes placed on opposite ends of the channel or network (24, 24') with a field generator (16), EO flow can be generated and controlled, and DEP manipulation of e.g. particles, beads, bubbles, cells, nanoparticles and/or nanotubes in the fluid can be generated (obtained).

The gradient in electric field within the device can be tuned in part by the potential applied by the field-generating device and in part by the relative dimensions of the channels in the fluidic system (e.g. the spacing between the pillars in an array) or constriction or expansion if a single channel is used. Tuning the gradient allows DEP manipulation to focus on a narrower range of particle type (e.g. bubbles rather than cells) or a restricted size of particles (e.g. all particles greater than 10 µm in diameter). Thus, the relative dimensions within the fluidic system and the electric field supplied must be tuned to individual applications.

Lab-on-a-Chip System

Further objects are to provide a microfluidic lab-on-a-chip system (200) for controlling liquid flow, comprising an electrokinetic fluid system (100, 100', 100") according to any the invention.

Still further objects are to provide a microfluidic lab-on-a-chip system (200) for controlling flow of charged or non-charged species, comprising an electrokinetic fluid system (100, 100', 100") according to any part of the invention.

Still further objects are to provide a microfluidic lab-on-a-chip system (200) for manipulating, transporting, and/or separating bubbles, cells or particles such as nanoparticles, nanotubes, or beads, comprising an electrokinetic fluid system (100) according to any part of the invention.

Uses

Further objects are to provide the use of an electrokinetic fluid system (100, 100', 100") according to the invention in a lab-on-a-chip system (LOC) (200).

Further objects are to provide the use of the electrokinetic fluid system (100, 100', 100") according to the invention for controlling liquid flow in a lab-on-a-chip system (200).

Still further objects are to provide the use of the electrokinetic fluid system (100, 100', 100") according to the invention for controlling flow of a charged or a non-charged species in a lab-on-a-chip system (200).

Further, said LOC-system may be combined with DEP-systems.

Further, said system of the invention (100, 100', 100") may, as described further herein, be combined with DEP-systems (300).

Thus, by the present invention is provided a system methods or the use of a system of the invention by which charged species such as e.g. ions, or non-charged species, e.g. sugar molecules, may be transported in a biological assay or system. E.g. the species may be transporter to a prokaryotic or eukaryotic cells, including tissue, cultivated or otherwise present on the target electrode or in the target electrolyte. By means of direct or indirect action, transported charged, e.g. ions, or non-charged species, may affect said cells and induce biological processes therein. Example of biological processes are cell activation or de-activation/inhibition/blocking that affect or influence intracellular processes such as e.g. phosphorylation cascades, proliferation, growth, apoptosis, adhesion, expression of cell surface markers both up- and down-regulation, etc., which are all measurable using assays and methods known in the art.

Accordingly, the present invention is useful in cell communication research, wherein said system can be utilized for delivering charged or non-charged species by means of a controlled flow of said species to cells in order to allow evaluation of the response of said cells.

The system of the invention may be used for stimulating a single cell using several different ionic or uncharged stimuli simultaneously or consecutively. In further embodiments, the system may be used for stimulating a single cell (i.e. a stimuli) with a spatial resolution which allows different portions of said single cell to be stimulated by different stimuli, such as said charged (e.g. ionic) or non-charged species.

The system may also be used to transport different species such as ions or molecules in the opposite direction, i.e. from a cell, e.g. in order to analyze molecular species, such as ionic species, that are excreted from a cell under certain conditions. In other words, the system according to the invention may be used as a means for delivery of species, such as charged or non-charged species, to cells, as well as a part of an arrangement for analyzing cellular response.

Said stimuli may turn on a cellular process or turn off a cellular process, or act as an inhibitor. A non-limiting example is potassium which may act as stimuli for neuronal cells by opening the voltage-operated $Ca^{2+}$ channels in the cell membrane. A non-limiting example of an inhibitor may be cadmium which may block the voltage-operated $Ca^{2+}$ channels in the cell membrane.

The term ion also encompasses molecular species that may be charged by setting a certain pH of the electrolyte liquid. The pH needed to charge these species may be calculated from the pKa of these species. The term ion also encompasses species which may be chemically modified to obtain a net charge, e.g. by attaching an ion to them.

The term ion may also encompass aggregate particles carrying a net charge, e.g. by emulsion of a given molecule by a surfactant species, either of which may carry charge. In addition, the cladding may comprise charged and uncharged species such that the net aggregate charge may be tailored.

Examples of such cladding materials include fatty acids, dodecylbenzene sulfonate, lecithin, and cetearyl alcohol.

The system of the present invention may be used to create concentration gradients of charged (e.g. ions) and non-charged species. Such concentration gradients may e.g. be useful in bioanalytical applications, such as cell signaling studies. Cell signaling studies include e.g. signaling between cells of the immune system, between neural cells or neural synapses or neural interconnections, or between stem cells or any other cells in the immune system, or tissue cell, including cells of the same kind or of two different kinds, normal cells or diseased cells, e.g. tumor cells or any other diseased cell involved in a disease relating to the CNS (central nervous system), or the brain, heart, etc. Cell signaling includes intracellular signaling events, and extracellular signaling events.

Thus, further embodiments are wherein the use of the electrokinetic fluid system (100, 100', 100") according to the invention for controlling flow of a charged or a non-charged species in a lab-on-a-chip system (200), wherein said species is a signal substance affecting stem cells. Stem cells include isolated stem cells or stem cell lines. Examples are neural stem cells, embryonic stem cells, adult stem cells.

Even further embodiments are wherein the use of the electrokinetic fluid system (100, 100', 100") according to the invention are for controlling flow of a charged or a non-charged species in a lab-on-a-chip system (200), wherein said species is a signal substance affecting neural cells.

Further, said cells may be human cells. In still a further embodiment, said cells are all human cells with the proviso of not being human embryonic stem cells. The cells may further be rodent cells such as rat, mouse, goat, cow, dog, feline etc. cells.

Still further embodiments are wherein use of the electrokinetic fluid system (100, 100', 100") according to the invention encompasses controlling flow of a charged or a non-charged species in a lab-on-a-chip system (200), wherein said species is an intracellular signal substance.

Still further uses are wherein said species is a signal substance affecting intracellular signaling.

The system of the present invention may be used to create oscillating ion or species concentrations close to the target electrode. Such oscillating ion concentration gradients mimic natural processes, and may e.g. be useful in bioanalytical applications.

The system of the present invention may further be useful in cell communication studies, wherein a cell may for example be stimulated by charged (e.g. ions) and non-charged species transported to the cell using the system and a cellular response may be studied or used by transporting secreted charged (e.g. ions) and non-charged species from a cell using the system.

The system of the present invention may further be used in connection with dielectrophoretic (300) manipulation of cells, particles, bubbles or other matter in the fluid. Such devices are useful for e.g. separating blood cells from whole blood, removing particulate contaminants from fluids, and manipulating nanoparticles or nanowires (dielectrophoretic field-flow fractionation). Dielectrophoresis (or DEP) is a phenomenon in which a force is exerted on a dielectric particle when it is subjected to a non-uniform electric field (see e.g. Brian J. Kirby, Micro- and Nanoscale Fluid Mechanics: Transport in Microfluidic Devices, 2009, chapter 17.1, http://www.kirbyresearch.com/textbook). This force does not require the particle to be charged. All particles exhibit dielectrophoretic activity in the presence of electric fields. However, the strength of the force depends strongly on the medium and particles' electrical properties, on the particles' shape and size, as well as on the frequency of the electric field. Consequently, fields of a particular frequency can manipulate particles with great selectivity. This has allowed, for example, the separation of cells or the orientation and manipulation of nanoparticles and nanowires.

Kits

Further objects provide a kit comprising the electrokinetic fluidic system (100) according to the invention, and, optionally, instructions for its use.

In some embodiments, a kit includes instructional materials disclosing, for example, means of use of the electrokinetic fluidic system (100) according to the invention, analysis/assays or means of use for a particular reagent. The instructional materials may be written, in an electronic form (e.g., computer diskette or compact disk) or may be visual (e.g., video files). The kits may also include additional components to facilitate the particular application for which the kit is designed. Thus, for example, the kit can include buffers and other reagents routinely used for the practice of a particular disclosed method. Such kits and appropriate contents are well known to those of skill in the art.

The kit may further comprise, in an amount sufficient for at least one assay, the electrokinetic fluidic system (100) according to the invention, as a separately packaged reagent.

Instructions for use of the packaged reagent are also typically included. Such instructions typically include a tangible expression describing reagent concentrations and/or at least one assay method parameter such as the relative amounts of reagent and sample to be mixed, maintenance time periods for reagent/sample admixtures, temperature, buffer conditions and the like.

Thus, the kit may further comprises instruction for its use as e.g. as a LOC-system in particular assays such as chemical assay systems or biological assay systems. Examples of chemical or biological assay systems are single cell analysis, PCR.

Still even further the kit may further comprise instruction for its use in a method according to the invention.

Certain kits may include a carrier means, such as a box, a bag, a satchel, plastic carton (such as moulded plastic or other clear packaging), wrapper (such as, a sealed or sealable plastic, paper, or metallic wrapper), or other container.

In some examples, kit components will be enclosed in a single packaging unit, such as a box or other container, which packaging unit may have compartments into which one or more components of the kit can be placed. In other examples, a kit includes a one or more containers, for instance vials, tubes, and the like that can retain, for example, one or more biological or chemical samples to be tested.

Other kits may include, for instance, syringes, cotton swabs, or latex gloves, which may be useful for handling, collecting and/or processing a biological or chemical sample. Kits may also optionally contain implements useful for moving a chemical or biological sample from one location to another, including, for example, droppers, syringes, and the like. Still other kit embodiments may include disposal means for discarding used or no longer needed items (such as samples, etc.). Such disposal means can include, without limitation, containers that are capable of containing leakage from discarded materials, such as plastic, metal or other impermeable bags, boxes or containers.

In one further embodiment, the system and/or kit of the invention is all-organic, i.e. all materials present in the system and kit are organic. One advantage of all-organic systems is that they may be more readily recycled than devices comprising a combination of organic and inorganic materials that may require disassembly prior to recycling.

In order to demonstrate the value of using conductive, electrochemically active materials for electrodes in microfluidic systems, poly(3,4-ethylenedioxythiophene)/poly(styrenesulfonate) (PEDOT:PSS) electrodes to induce an electroosmotic flow (EOF) through a glass capillary have been created.

PEDOT:PSS electrodes are shown to have a smaller impact on electrolyte pH, e.g. cause a smaller change than traditional metal electrodes, during the electrochemical reactions needed to maintain an electric field in the capillary due to the fact that the redox reaction involves the electrode material instead of on the electrolyte. Once the electrode material is consumed, the reaction can only involve the electrolyte. When in contact with an electrolyte, the switching of PEDOT:PSS between the p-doped and undoped state or vice versa is compensated by ions leaving or entering the PEDOT:PSS polymer, since the PEDOT:PSS effectively acts as an electron-to-ion transducer. This allows an electrochemical reaction to take place at each electrode without causing hydrolysis, gas bubbles and other by-products that are normally found when the electrolyte, e.g. water, is hydrolyzed on traditional metal electrodes. The use of electrochemically active electrodes enables the production of LOC devices able to transport biomolecules, cells and other pH- and redox-sensitive species in a controlled manner using the uniform velocity profile found in EOF devices.

Due to the electrochemical reactions taking place at each electrode during operation of the electrokinetic fluid system, the electrode material will be consumed (fully doped (oxidized) at the anode or fully dedoped (neutral) at the cathode). Thus, the electrokinetic fluid system can not be operated in one direction indefinitely. In one implementation of the electrodes described here, the system is intended to be used only once, and reversibility of the electrochemistry of the electrodes is not an issue. In the further implementations, a material such as PEDOT:PSS, which can be repeatedly oxidized and reduced, is used in the electrodes, allowing for current to be driven first in one direction, and then the other when the potential is reversed. Reversing the process in this manner effectively regenerates the consumed electrodes. This process can be repeated in a cyclic fashion thousands of times.

However, when one or both electrodes are fully consumed, i.e. p-doped or dedoped (undoped, i.e. fully reduced to the neutral state) at the anode or cathode, respectively, hydrolysis of the electrolyte, e.g. water, at the electrode/electrolyte interface takes over and the electrokinetic fluid system continues to operate in a manner similar to a conventional electroosmotic pump or a conventional electrophoretic system having metal electrodes.

In order to avoid electrochemical reactions in the electrolyte, it is important to design and operate the inventive electrokinetic fluid system in a manner such that the electrodes are never fully consumed. This can be accomplished by periodically reversing the direction of the flow within the electrokinetic fluid system or by over-dimensioning the electrodes compared to the volume and concentration of the electrolyte to be transported so that they are never consumed. For example, if electrodes, each made from 1 gram of PEDOT:PSS, would be consumed by moving 10 mL of water in a given pump configuration with a given electrolyte concentration, using 2 or more grams of PEDOT:PSS in each electrode would prevent the PEDOT from being fully consumed, and prevent hydrolysis.

The present invention also relates to a method for manufacturing an inventive electrode.

According to an embodiment, a generalized method for manufacturing an electrode comprises the steps of:
- applying a conductive, electrochemical active electrode material to a substrate;
- possibly, adding a dopant to or using electrochemistry on the electrode in order to increase the conductivity and to change the state of the electrode;
- possibly, adding an electronic contact enhancing substance to a part of the surface of the electrode in order to facilitate electronic contact to the instrumentation, e.g. to the electric field generating equipment.

As revealed above, pi-conjugated polymers are suitable for the purpose of the system according to the invention and further described herein.

The substrate can be the same material (e.g. plastic or glass such as a capillary) from which the pump or separation device is manufactured. The substrate can be a separate material, such as glass or plastic, which is placed into a pump or separation device for use.

The substrate onto which the system according to the invention may be fabricated preferably is electrically and ionically insulating and may comprise rigid materials such as Si wafers with an insulating oxide (SiOx) or nitride layer (Si3N), glass wafers such as pyrex wafers, glass substrates, such as microscope slides, plastic substrates such as PET, polystyrene, used in petri dishes, and ceramics. The substrates may also be flexible such as plastic films, Orgacon™ films (both plastic and paper), or paper based materials.

The system according to the invention is also particularly advantageous in that it can be easily realized on a support, such as polymer film or paper. Thus, the different components can be deposited on the support by means of conventional printing techniques such as screen printing, offset printing, gravure printing, ink-jet printing and flexographic printing, or coating techniques such as knife coating, doctor blade coating, extrusion coating and curtain coating, such as described in "Modern Coating and Drying Technology" (1992), eds E D Cohen and E B Gutoff, VCH Publishers Inc, New York, N.Y., USA. In the embodiments of the invention that utilize a conductive polymer material in the electrodes and/or ion-conductive channel (ion channel), this material can also be deposited through in situ polymerization by methods such as electropolymerization, UV-polymerization, thermal polymerization and chemical polymerization in the liquid or vapor phase.

As an alternative to these additive techniques for patterning of the components, it is also possible to use subtractive techniques, such as local destruction of material through chemical or gas etching, by mechanical means such as scratching, scoring, scraping or milling, or by any other subtractive methods known in the art. An aspect of the invention provides such processes for the manufacture of a system from the materials specified herein.

Thus, in one embodiment of the system, said electrodes and said channel (14) are directly or indirectly attached to a solid support such as glass or to a flexible support such as polymer film or paper.

The system according to the invention may preferably be encapsulated, in part or entirely, for protection of the device. The encapsulation retains any solvent needed for e.g. the liquid e.g. the electrolyte to function, and also keeps oxygen from disturbing the electrochemical reactions in the device. Encapsulation can be achieved through liquid phase processes. Thus, a liquid phase polymer or organic monomer can be deposited on the device using methods such as spray-coating, dip-coating or any of the conventional printing techniques listed above. After deposition, the encapsulant can be hardened for example by ultraviolet or infrared irradiation, by solvent evaporation, by cooling or through the use of a two-component system, such as an epoxy glue, where the components are mixed together directly prior to deposition. Alternatively, the encapsulation is achieved through lamination of a solid film onto the ion transport device. In preferred embodiments of the invention, in which the components of the system are arranged on a support, this support can function as the bottom encapsulant. In this case encapsulation is made more convenient in that only the top of the sheet needs to be covered with liquid phase encapsulant or laminated with solid film.

The system according to the invention may also be manufactured using conventional semiconductor processes, such as photolitography and etching. When such methods are used, the electrode material(s) may preferably be deposited onto the substrate using any suitable deposition method, e.g. printing or lamination. The substrate carrying the electrode material(s) may then be patterned using conventional photoresist/etching techniques.

The system according to the invention may also present further features, which facilitate use of the system. Such features include for example terminals for connecting a voltage source to the electrodes of the system, means for encapsulating the system in order to make it more robust to handling, and to prevent evaporation or contamination of liquid electrolytes.

The electrodes of the system may be arranged such that liquid electrolytes may be deposited directly onto the desired electrodes.

The system according to the invention may further comprises means for retaining an electrolyte in the system, arranged such that the electrolyte is in contact with the desired electrodes. Thus, in one embodiment the device comprises means for retaining said electrolytes.

The electrolytes may be confined to a certain area of the system by means of one or more physical or chemical confinement methods. The electrolytes may for example be confined by walls or the like arranged on the system surface, by openings in a partial encapsulation of the system as described herein, or by suitable chemical or physical treatment of the system surface, such as rendering the surface partially hydrophobic, e.g. using a fluorinated coating.

For example, he electrolyte may be retained in the system by means of a container, arranged such that the electrolytes are in contact with the desired electrode(s). Said container may be made of glass or a polymer material, but other materials may also be used. The container may be open or partly or fully sealed.

Said means or container for retaining electrolytes in the system may be wherein the surface of said container is biocompatible.

The system according to the invention may further comprise means for measuring the amount of species, such as charged or non-charged molecules, being transported at least one first to at least one second electrode (10, 10') by measuring the current.

According to an example, a method for manufacturing a PEDOT:PSS electrode comprises the steps of:
  drop-casting 100 μl PEDOT:PSS (1.3 wt % dispersion in $H_2O$, with 0.5% PEDOT and 0.8% PSS, conductive grade, Sigma-Aldrich) containing 5% diethylene glycol (Sigma-Aldrich) on a roughened OH-film substrat;
  drying the PEDOT:PSS; and
  adding stripes of silver paint to the edge of the PEDOT:PSS electrode that is not in contact with the electrolyte to facilitate electronic contact to the instrumentation, e.g. to the electric field generating equipment.

In further embodiments, the film may be added in one of many methods, including printing techniques (e.g. inkjet printing), coating techniques (spin coating, doctor blading, etc.), or even polymerized (electrochemically or chemically) in-situ. Further, it may not be necessary to add conductive material to contact the polymer/metal oxide used.

FIG. 4 schematically illustrates an embodiment of a microfludic lab-on-a-chip (LOC) system 200 comprising an electrokinetic fluid system 100 according to the invention.

Even if the present invention has been described in relation to a microfluidic lab-on-a-chip device, it should be understood that the inventive electrodes and the inventive electrokinetic fluid system can be used in e.g. a laboratory or a large-scale application. For example, the electrokinetic fluid system according to the present invention could also be used in laboratory-scale or industrial-scale capillary electrophoresis separation systems, large-scale electroosmotic pumps.

EXAMPLES

Example 1

Example of Electroosmotic Pump with PEDOT:PSS

Figure 5A:
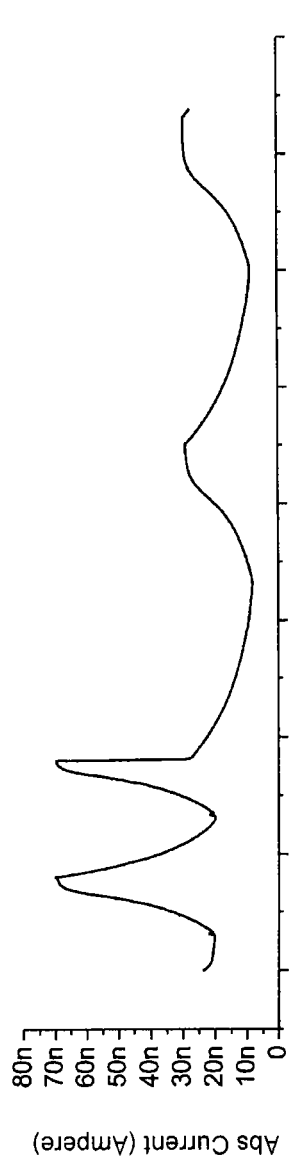

An exemplary electroosmotic pump has been manufactured by placing a capillary 14, e.g. a silica capillary, having an inner diameter between about 25 μm and about 75 μm, between two vessels 12, 12' in a 128×86×12 mm (lwh) 8-well (each well is 40×30×12 mm) 2-3 cm-wide plastic dish. The pump occurs across the 30 mm wall. Each well contained a liquid electrolyte, 5-50 mM $NaH_2PO_4$ with pH 9. A PEDOT:PSS electrode 10, 10' on a PET film was arranged in each vessel by submersing a portion of the PEDOT:PSS electrode in the electrolyte, and a potentials of up to 10V were applied between the electrodes by means of an electric field generator 16. Filling the two vessels 12, 12' with salt solutions of different concentrations allowed the inventors to measure the flow rate through the capillary 14 indirectly via displacement without the use of additives, as the current transported through the capillary is proportional to the concentration of the electrolyte within the capillary. Thus, when the capillary, initially filled with the electrolyte of low concentration, begins to be filled with the high-concentration electrolyte by the action of the pump, the current measured through the device increases with time as shown in FIG. 5A. Similarly, the displacement of the high-concentration electrolyte in the capillary by low-concentration electrolyte (when the flow is reversed) causes a decrease in current. The flow velocity can then be deduced from the slope of the resistance curve (shown in FIG. 5B). For a more detailed description of the technique used for measuring the flow velocity, see Electrophoresis 2004, 25, 3687-3693.

Two wells (40×30×12 mm) filled with 7 ml of 5 mM and 20 mM $Na_2HPO_4$ pH 9. Wells connected with a 10 mm fused silica capillary with an inner diameter of 25 μm. One PEDOT:PSS electrode partially submerged into solution in each well, electrode in 5 mA well connected to + and electrode in 20 mM well connected to − of the Kiethley 2636A SourceMeter. SourceMeter applies different potentials while current is measured.

Results

Figure 5B:
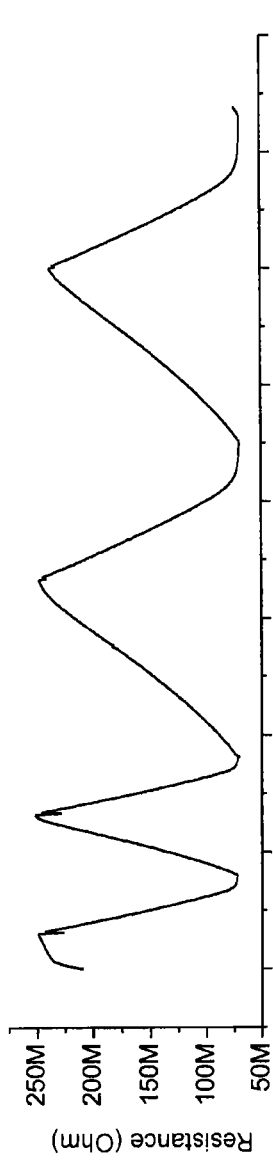
Figure 5C:
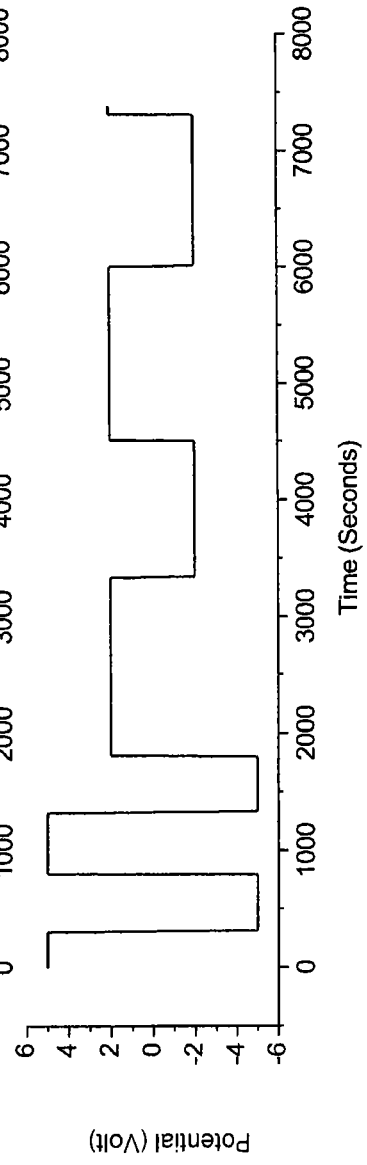

When a potential of +5 V was applied between the electrode the pump moved electrolyte from the 25 mM well to the 5 mM well, resulting in a current of 70 nA corresponding to a resistance across the capillary of 70 MΩ. When a potential of −5 V was applied the pump moved electrolyte from the 5 mM well to the 25 mM well, displacing the 25 mM electrolyte in the capillary volume resulting in a current of 20 nA corresponding to a resistance of 250 MΩ. Complete displacement of fluid occurred in about 8 min, total charge transferred during displacement was around 20 μC. Switching between +2 V and −2 V potential the displacement of fluid changes the current between 8.5 nA and 29 nA, corresponding to a capillary resistance between 235 MΩ and 68 MΩ. The fluid displacement velocity 20 μm/s for a potential of 5 V and 7 μm/s for a potential of 2 V. See FIG. 5A-C showing Abs Current, resistance and potential.

Example 2

Further Exemplary Electroosmotic Pump

An electroosmotic pump comprising two vessels filled with an ionic solution, each vessel containing a PEDOT:PSS electrode and connected with a fused silica capillary functioning as a passageway between the vessels. One end of the electrode was submerged into the solution and the opposite end above surface connected to the electric field generator. The capillary was about 10 mm long and had an inner diameter in the range of about 25-75 μm. An electroosmotic flow was generated inside the capillary by applying a potential between the electrodes. The potential was selected to be in the range of about 1-100 V. Fluid movement was verified with a displacement setup where the two vessels had different ion concentrations, about 5 and about 22 mM of $Na_2HPO_4$, respectively, and the current through the capillary was monitored with a Keithley 2636A SourceMeter.

Results

For a 25 μm capillary the fluid displacement velocity was 20 μm/s for a potential of 5 V and 7 μm/s for 2 V. This value is similar to the velocity in standard electrophoresis setups.

FIG. 3 schematically illustrates an embodiment of an electrokinetic fluid system 100 in the form of an electrokinetic separation system 100" such as an electrophoretic system 100". As schematically illustrated, the electrophoretic system 100" comprises two electrodes 10, 10' arranged in a respective vessel 12, 12'. Further, a channel 14, e.g. a capillary, is arranged as a passageway between the two vessels 12, 12', by means of which channel 14 solid particles 18, e.g. sample particles or charged species such as a molecule, can be transported between the vessels 12,12' when an electric field is applied over the electrodes 10,10'. The electric field being generated by means of an electric field generator 16 connected to the electrodes. A detector 20 can be arranged at the channel 14 in order to detect characteristics of the sample 18 to be analyzed and transported in the channel 14.

While the electrophoretic system 100" is configured to separate charged species, e.g. ions or particles based on their movement under the influence of an applied electric field, it should be understood that the electric field applied in order to separate the species also gives rise to an electroosmotic flow, i.e. to a fluid flow, in the channel 14.

Example 3

Operating the Electrodes at Low Voltage

In this example, an electrode such as those used in the system of Example 2 is shown to operate at low voltage. The electrode is a pi-conjugated polymer, namely PEDOT:PSS. Its performance, as the working electrode in a three-electrode configuration connected to a potentiostat (μAutolab by Metrohm) with a Ag/AgCl reference electrode and a Pt counter electrode, is compared to a similar experiment with a Pt electrode as the working electrode.

FIG. 6 shows the results in a cyclic voltammogram for platinum (Pt, dotted line) and PEDOT:PSS (solid line) electrodes in 20 mM $NaCl_{(aq)}$. Arrows show the oxidation and reduction peaks associates with PEDOT. It should be pointed out that the PEDOT:PSS electrode (solid line) always shows a current in this experiment, but the Pt-electrode shows almost no current when −0.8 V<E<1.2 V. E is the potential applied relative to the Ag/AgCl reference electrode.

The result in FIG. 6 demonstrates that, when used in the microfluidic system, a pair of PEDOT:PSS electrodes can pass a Faradaic current even at small applied potentials (e.g. <1V) while a pair of Pt electrode passes very little current for potentials less than about 2V (the voltage difference between the oxidation and reduction peaks of water on Pt, as shown in FIG. 6).

Example 4

Example of Electroosmotic Pump with Polypyrrole (PPy)

An exemplary electroosmotic pump has been manufactured by placing a capillary 14, e.g. a silica capillary, having an inner diameter of 25 µm, between two vessels 12, 12' in a 128×86×12 mm (lwh) 8-well (each well is 40×30×12 mm) 2-3 cm-wide plastic dish. The pump occurs across the 30 mm wall. Each well contained a liquid electrolyte, 5-20 mM NaCl with pH 5.7. A PPy electrode 10, 10' on a PET film was arranged in each vessel by submersing a portion of the PPy electrode in the electrolyte, and potentials of up to 10V were applied between the electrodes by means of an electric field generator 16. Filling the two vessels 12, 12' with salt solutions of different concentrations allowed the inventors to measure the flow rate through the capillary 14 indirectly via displacement without the use of additives, as the current transported through the capillary is proportional to the concentration of the electrolyte within the capillary. For a detailed description of measuring the flow velocity via this technique, see the description in Example 1, or Electrophoresis 2004, 25, 3687-3693.

The polypyrrole electrodes were produced by performing vapor phase polymerization onto pieces of transparency film. An oxidation source of 58 mg $FeCl_3$ dissolved in 150 µl methanol was spin-coated onto 50×50 cm pieces of roughened transparency film. Once dry, the film was suspended with the coated side facing downward over an open beaker containing pyrrole monomer. The entire setup was enclosed in another beaker. Polymerization occurs when the monomer evaporates and reaches the $FeCl_3$ oxidant on the transparency film. A slow flow of nitrogen gas, while heating the beaker to 50° C., makes the polymerization occur in less than 10 min. The film was then washed with ethanol/water and dried before cutting it into 20×30 mm electrodes. Finally, silver paint was applied to one edge for easy connection of the polymer electrode to instrumentation. For a detailed description of the PPy vapor phase polymerization technique used, see *Vapor Phase Polymerization of Pyrrole and Thiophene Using Iron (III) Sulfonates as Oxidizing Agents*, Bjørn Winther-Jensen, Jun Chen, Keld West, and Gordon Wallace, *Macromolecules*, 2004, 37 (16), pp 5930-5935 (DOI: 10.1021/ma049365k http://pubs.acs.org/doi/abs/10.1021/ma049365k)

Two wells (40×30×12 mm) were filled with 10 ml of 5 mM and 20 mM NaCl, respectively, pH 5.7 in both cases, connected with a 10 mm fused silica capillary with an inner diameter of 25 µm. Each well contains one PPy electrode partially submerged into solution: the electrode in the 5 mM well connected to the positive terminal and the electrode in 20 mM well connected to negative terminal of the Kiethley 2636A SourceMeter. The SourceMeter applies pre-programmed potentials while measuring the current through the system.

Results

When a potential of +10 V was applied between the electrode the pump moved electrolyte from the 20 mM well to the 5 mM well, resulting in a current of 270 nA corresponding to a resistance across the capillary of 36 MΩ. When a potential of −10 V was applied the pump moved electrolyte from the 5 mM well to the 20 mM well, displacing the 20 mM electrolyte in the capillary volume resulting in a current of 80 nA corresponding to a resistance of 120 MΩ. Complete displacement of fluid occurred in about 13 min, total charge transferred during displacement was around 150 µC. This corresponds to a fluid displacement velocity 12 µm/s for a potential of 10 V.

Example 5

Example of Electroosmotic Pump with Polyaniline (PANI)

An exemplary electroosmotic pump has been manufactured by placing a capillary 14, e.g. a silica capillary, having an inner diameter of 25 µm, between two vessels 12, 12' in a 128×86×12 mm (lwh) 8-well (each well is 40×30×12 mm) 2-3 cm-wide plastic dish. The pump occurs across the 30 mm wall. Each well contained a liquid electrolyte, 5-20 mM NaCl with pH 5.7. A PANI electrode 10, 10' on a PET film was arranged in each vessel by submersing a portion of the PANI electrode in the electrolyte, and potentials of up to 10V were applied between the electrodes by means of an electric field generator 16. Filling the two vessels 12, 12' with salt solutions of different concentrations allowed the inventors to measure the flow rate through the capillary 14 indirectly via displacement without the use of additives, as the current transported through the capillary is proportional to the concentration of the electrolyte within the capillary. See the description found in Example 1 for more details, or Electrophoresis 2004, 25, 3687-3693.

The polyaniline electrodes were produced drop casting polyaniline in xylene onto pieces of transparency film. A total of 400 µl polyaniline (5 weight %) in xylene was drop cast on a 60×25 mm pieces of roughened transparency film. Once dry the film was washed in water and then submerged into 20 mM NaCl with 0.18 weight % polystyrene sulfonic acid. The film was washed in water and dried with a flow of nitrogen gas and then cut into 15×5 mm electrodes. Finally silver paint is applied to one edge for easy connection of the polymer electrode to instrumentation.

Two wells (40×30×12 mm) filled with 10 ml of 5 mM and 20 mM NaCl pH 5.7. Wells connected with a 10 mm fused silica capillary with an inner diameter of 25 µm. Each well contains one PPy electrode partially submerged into solution, electrode in 5 mA well connected to + and electrode in 20 mM well connected to − of the Kiethley 2636A SourceMeter. SourceMeter applies different potentials while current is measured.

Results

When a potential of +10 V was applied between the electrode the pump moved electrolyte from the 20 mM well to the 5 mM well, resulting in a current of 100 nA corresponding to a resistance across the capillary of 100 MΩ. When a potential of −10 V was applied the pump moved electrolyte from the 5 mM well to the 20 mM well, displacing the 20 mM electrolyte in the capillary volume resulting in a current of 33 nA corresponding to a resistance of 300 MΩ. Complete displacement of fluid occurred in about 5 min, total charge transferred during displacement was around 20 µC. This corresponds to a fluid displacement velocity 37 ηm/s for a potential of 10 V. Calculated flow velocity for potentials between 5 and 80 V are shown in table 1.

TABLE 1

| Potential | Flow velocity |
|---|---|
| 80 V | 290 µm/s |
| 40 V | 140 µm/s |
| 20 V | 70 µm/s |

TABLE 1-continued

| Potential | Flow velocity |
|---|---|
| 10 V | 37 μm/s |
| 5 V | 17 μm/s |

Example 6

Example of EO Pump Combined with Dielectrophoretic Focusing with PEDOT:PSS Electrodes An exemplary device for dielectrophoretic focusing has been manufactured by bonding together a 30 mm long by 20 mm wide by 0.7 mm thick piece of patterned PDMS 20 and a microscope slide 21 that was 72 mm by 26 mm by 1 mm, see FIG. 9. Note that holes, electrodes, channels and total device thickness have been scaled up a factor 2 for easier viewing. The PDMS pattern was produced using soft lithography by pouring 2 g of 1:10 dimethylsiloxan/curing-agent (Sylgard 184, Dow Corning Corporation) mixture onto a 100 mm diameter silica wafer with a 25 μm high SU-8 pattern and placing the covered wafer in a 100° C. oven for 2 hours. This SU-8 pattern contained 50 μm by 2000 μm holes (25 μm deep), which result in similarly sized "pillars" of PDMS in the final device. PDMS was removed from the silica wafer and the desired pattern cut out and two holes 22 were made 4 mm apart with a 5 mm biopsy punch (Miltex). A thin film of 1:10 dimethylsiloxan/curing-agent was applied on the patterned side of the PDMS except in a 2 mm wide and 3 mm long strip 23 between the two holes. The PDMS piece and a clean microscope slide were air plasma-treated (Deiner Electronic, Pico plasma cleaner) for 1 min at 0.1 mBar, with removable tape (3M) covering the whole PDMS piece except the strip and holes. Directly after plasma treatment the tape was removed and the two pieces pressed together.

PEDOT electrodes were produced by drop casting PEDOT:PSS on transparency film. The transparency film (M3) was roughened with sandpaper (P240, average particle diameter 58 μm) and cut into pairs of either 2×5 mm or 3×7 mm pieces. A mixture of PEDOT:PSS (1.2 weight % in water, Sigma Aldrich) with 1% diethylene glycol (Sigma Aldrich) was then drop casting 10 μl/20 μl onto the 2×5/3×7 mm electrodes and left to dry overnight in room temperature. One end of each piece was covered with a 1 mm strip of silver paint (Electrolube) to facilitate instrument connection. Any uncoated areas at the ends of the electrodes were cut away.

The device was placed under a microscope (Carl Zeiss, Axiovert 200M) and two 2×5 mm electrodes 24 were connected via mini-crocodile-clips to a Keithley 2636 SourceMeter 16 and placed in the PDMS holes 23. The wells created by the PDMS holes were filled with 15 μl of 20 mM NaCl containing 0.02 weight % of 5 μm polystyrene micro particles (Fluka), filling up the channels created by the patterned 2×4 mm strip between the wells directly. The wells were balanced with pure 20 mM NaCl to reduce pressure driven flow in the channels. During the measurement pictures were taken while applying either a constant (DC) or sinus-like (stepwise AC) between 0-200 V.

Results

When applying a DC potential, the movement of the spheres as observed in a microscope clearly shows the electroosmotic flow inside the channel between the plasma-treated PDMS and glass. The DC potential was used to pump precisely and reduces the pressure-driven flow between wells, which made observing the dielectrophoretic focusing easier.

FIG. 10A shows a 4-way intersection of channels 25 where the wells containing electrodes are to the left and right, as seen in the zoomed out FIG. 11B. When applying a potential between the electrodes the electric field will primarily be horizontal (left-right) with a smaller difference vertically (up-down). According to the theory of dielectrophoresis (see e.g. Pohl, H. A., 1978. *Dielectrophoresis the behavior of neutral matter in nonuniform electric fields*. Cambridge University Press. Cambridge) an insulating material in an electric field will be polarized and a polarized particle will experience a force if there is a gradient in the electric field. Since there is a difference in electric-field-gradient between moving up-down and right-left our insulating polystyrene particles should be forced into the same place when a field is applied. However, if we apply a strong DC field we will simply pump everything away due to the electroosmotic flow, so the applied potential needs to be AC-like.

In this measurement we used a 64-step approximation to a "sinus-wave" generated by a Kiethley 2636 source-meter resulting in a periodic frequency of approximately 70 Hz. The microscope camera (Carl Zeiss, AxioCam HRc) was connected to a PC and images were taken manually every 5 or 10 seconds. The pattern of the PDMS was of 50×2000 μm rectangles in the left-right direction 26 with 50 μm wide channels running between them, see FIG. 10B. When no potential was applied, the 5 μm polystyrene particles 27 spread out and moved slowly with the pressure driven flow (caused by evaporation at the wells), see FIG. 10C. When the AC potential was applied, the particles oscillated, often pairing up, and when migrating toward intersections of open channels and the vertical walls where the electric field was expected to be smallest, see FIG. 10D. After removing the potential, the particles drifted away from the walls and one another, but could be recaptured by applying the AC signal again. The ability to capture the polystyrene particles at specific positions in a microfluidic system, the vertical walls in this case, demonstrates that these electrodes can be used for dielectrophoretic focusing.

The invention claimed is:

1. An electrokinetic fluidic system for controlling liquid flow, comprising:
   a) a first and a second electrode arranged in a respective vessel, said electrodes comprising a conductive, electrochemically active electrode material selected from a pi-conjugated polymer-based material and a metal oxide material, said electrode material being adapted to be subjected to an electrochemical reaction when in use in said electrokinetic fluidic system, and
   b) a channel arranged as a passageway between the two vessels, said channel allowing flow of electrolyte between said two vessels,
   wherein the fluidic system is designed such that during said electrochemical reaction the pH of the electrolyte is constant or almost constant and there is a gas bubble free environment at said first and second electrode, and
   wherein said channel is a porous material of solid or semi-solid material allowing flow of electrolyte.

2. The electrokinetic fluidic system according to claim 1 wherein the conductive, electrochemically active electrode material conducts electricity in at least one reduction-oxidation state, is electrochemically switchable, does not break apart and does not release toxic substances into the electrolyte.

3. The electrokinetic fluidic system according to claim 1 wherein the conductive, electrochemically active electrode material is selected from the group consisting of polyacetylenes, polypyrroles, polythiophenes, polyanilines, poly(p-phenylene sulfide), poly(p-phenylene vinylene)s, polyindole, polypyrene, polycarbazole, polyazulene, polyazepine, polyfluorenes, polynaphthalene, polyisothianaphthalenes, a copolymer thereof, and a mixture thereof.

4. The electrokinetic fluidic system according to claim 1, wherein said channel is at least one capillary allowing flow of electrolyte.

5. The electrokinetic fluidic system according to claim 1, wherein the walls of said channel are charged.

6. The electrokinetic fluidic system according to claim 1, wherein said channel is <200 µm in diameter.

7. The electrokinetic fluidic system according to claim 1, further comprising an electric field generating device.

8. The electrokinetic fluidic system according to claim 1 wherein the system forms at least a part of a lab-on-a chip for controlling fluidic flow.

9. The electrokinetic fluidic system according to claim 1 wherein the system forms at least a part of a lab-on-a chip for controlling flow of one or more charged or non-charged species.

10. An electrokinetic fluidic system for controlling liquid flow, comprising:
   a) a first and a second electrode arranged in a respective vessel, said electrodes comprising a conductive, electrochemically active electrode material selected from a pi-conjugated polymer-based material and a metal oxide material, said electrode material being adapted to be subjected to an electrochemical reaction when in use in said electrokinetic fluidic system,
   b) a channel arranged as a passageway between the two vessels, said channel allowing flow of electrolyte between said two vessels, and
   c) a dielectrophoretic system,
   wherein the fluidic system is designed such that during said electrochemical reaction the pH of the electrolyte is constant or almost constant and there is a gas bubble free environment at said first and second electrode.

11. The electrokinetic fluidic system according to claim 10 wherein the conductive, electrochemically active electrode material conducts electricity in at least one reduction-oxidation state, is electrochemically switchable, does not break apart and does not release toxic substances into the electrolyte.

12. The electrokinetic fluidic system according to claim 10 wherein the conductive, electrochemically active electrode material is selected from the group consisting of polyacetylenes, polypyrroles, polythiophenes, polyanilines, poly(p-phenylene sulfide), poly(p-phenylene vinylene)s, polyindole, polypyrene, polycarbazole, polyazulene, polyazepine, polyfluorenes, polynaphthalene, polyisothianaphthalenes, a copolymer thereof, and a mixture thereof.

13. The electrokinetic fluidic system according to claim 10, wherein said channel is at least one capillary allowing flow of electrolyte.

14. The electrokinetic fluidic system according to claim 10, wherein said channel is a porous material of solid or semi-solid material allowing flow of electrolyte.

15. The electrokinetic fluidic system according to claim 10, wherein the walls of said channel are charged.

16. The electrokinetic fluidic system according to claim 10, wherein said channel is <200 µm in diameter.

17. The electrokinetic fluidic system according to claim 10, further comprising an electric field generating device.

18. The electrokinetic fluidic system according to claim 10 wherein the system forms at least a part of a lab-on-a chip for controlling flow of one or more charged or non-charged species.

19. An electrokinetic fluidic system for controlling liquid flow, comprising:
   a) a first and a second electrode arranged in a respective vessel, said electrodes comprising a conductive, electrochemically active electrode material selected from a pi-conjugated polymer-based material and a metal oxide material, said electrode material being adapted to be subjected to an electrochemical reaction when in use in said electrokinetic fluidic system,
   b) a channel arranged as a passageway between the two vessels, said channel allowing flow of electrolyte between said two vessels, and
   c) a dielectrophoretic system,
   wherein the fluidic system is designed such that during said electrochemical reaction the pH of the electrolyte is constant or almost constant and there is a gas bubble free environment at said first and second electrode, and
   wherein the system forms at least a part of a lab-on-a chip for controlling flow of one or more charged or non-charged species.

20. The electrokinetic fluidic system of claim 19 wherein the system is arranged for manipulation of particles in a fluid.

* * * * *